United States Patent [19]

Butler et al.

[11] Patent Number: 5,417,009

[45] Date of Patent: * May 23, 1995

[54] HOUSE FLY, HORN FLY, AND MOSQUITO REPELLENTS AND APPARATUS USEFUL IN TESTING EFFICACY OF SAME

[75] Inventors: Jerry F. Butler, Gainesville, Fla.; Anna B. Marin, Leonardo, N.J.; Craig B. Warren, Rumson, N.J.; Richard A. Wilson, Westfield, N.J.; Braja D. Mookherjee, Holmdel, N.J.

[73] Assignees: International Flavors & Fragrances Inc., New York, N.Y.; The University of Florida, Gainesville, Fla.

[ * ] Notice: The portion of the term of this patent subsequent to Apr. 27, 2010 has been disclaimed.

[21] Appl. No.: 130,398

[22] Filed: Oct. 1, 1993

Related U.S. Application Data

[60] Continuation-in-part of Ser. No. 982,374, Nov. 25, 1992, Pat. No. 5,281,621, which is a continuation-in-part of Ser. No. 789,695, Nov. 8, 1991, abandoned, which is a division of Ser. No. 643,206, Jan. 18, 1991, Pat. No. 5,126,369.

[51] Int. Cl.$^6$ .............................................. A01M 1/04
[52] U.S. Cl. ...................................................... 43/113
[58] Field of Search ................... 43/113, 107, 122, 139

[56] References Cited

U.S. PATENT DOCUMENTS

| 5,205,065 | 4/1993 | Wilson | 43/113 |
| 5,228,233 | 7/1993 | Butler | 43/113 |
| 5,255,468 | 10/1993 | Cheshire, Jr. | 43/113 |
| 5,301,458 | 4/1994 | Deyores et al. | 43/113 |
| 5,327,675 | 7/1944 | Butler et al. | 43/113 |

*Primary Examiner*—Kurt Rowan
*Attorney, Agent, or Firm*—Arthur L. Liberman

[57] ABSTRACT

An apparatus for trapping insects having a radiation means and a semiochemical attractant means such that insects enter an air stream and are carried into a housing to trap them. The device further contains radiation pulsing means and a power supply to power a motor which drives a propeller to induce a flow of air into the trap.

6 Claims, 23 Drawing Sheets

FIG.2-A
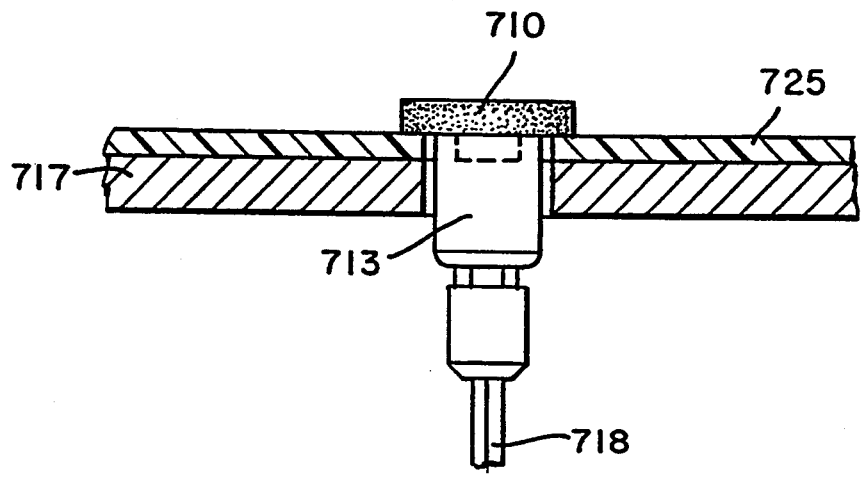
FIG.3-A
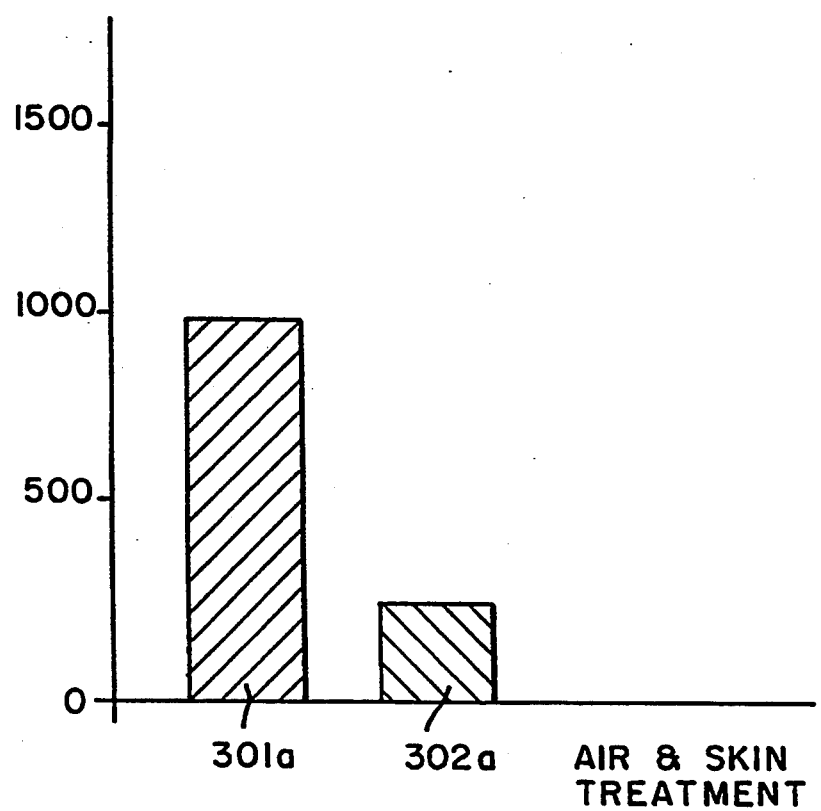

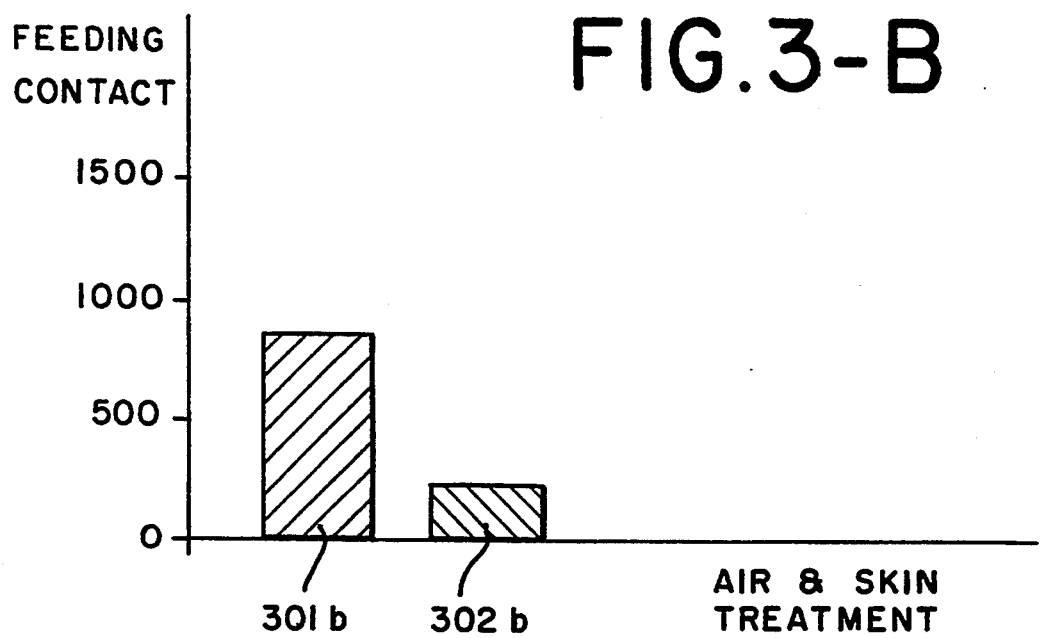
FIG. 3-B
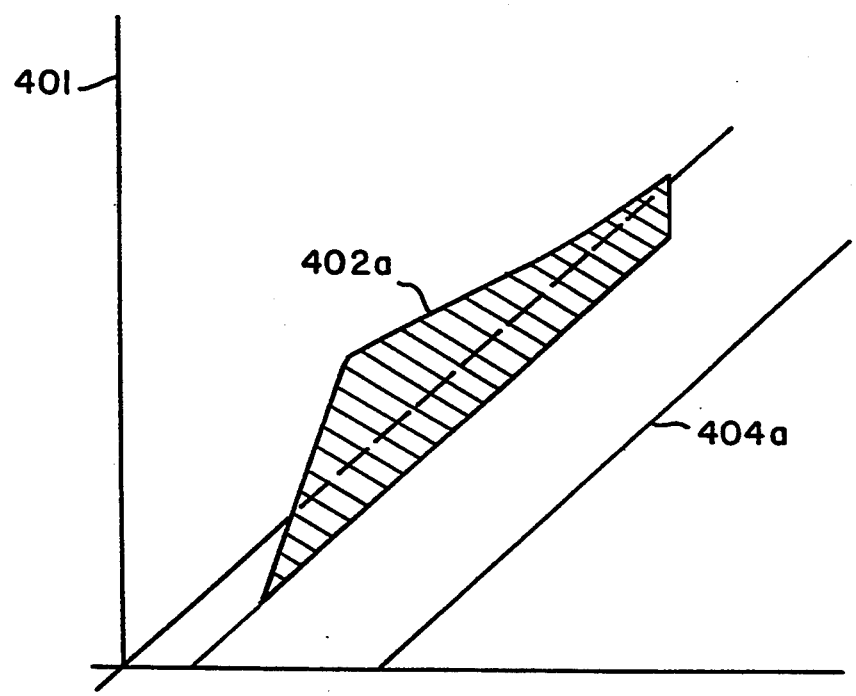
FIG. 4-A

FIG.4-B
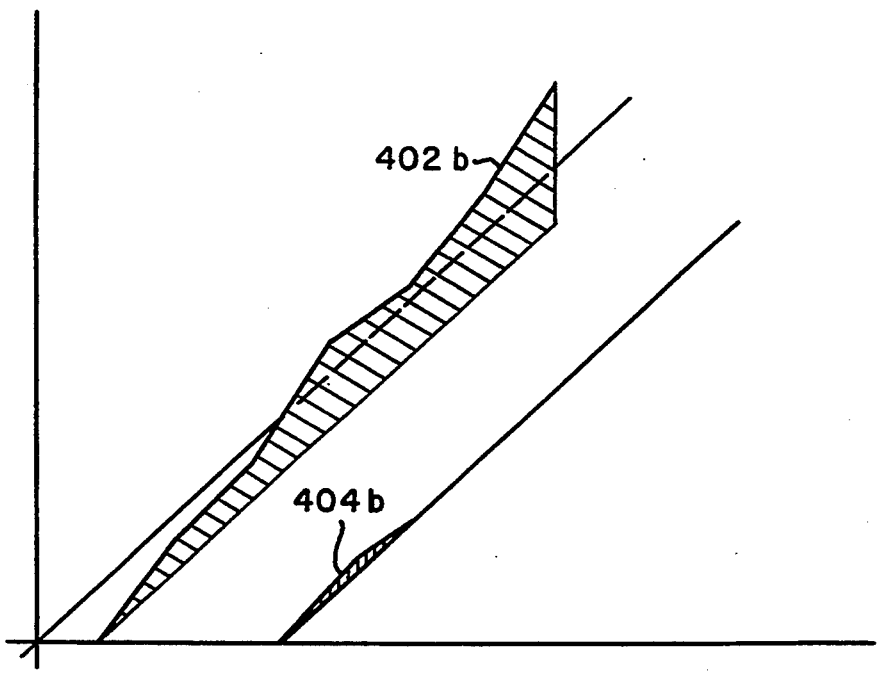
FIG.4-C
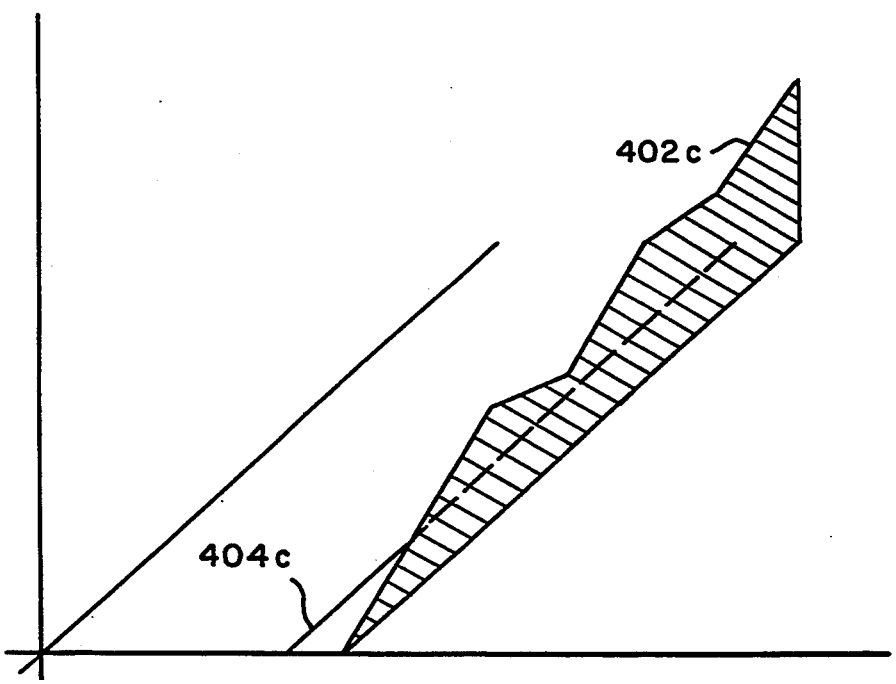

FIG.4-D
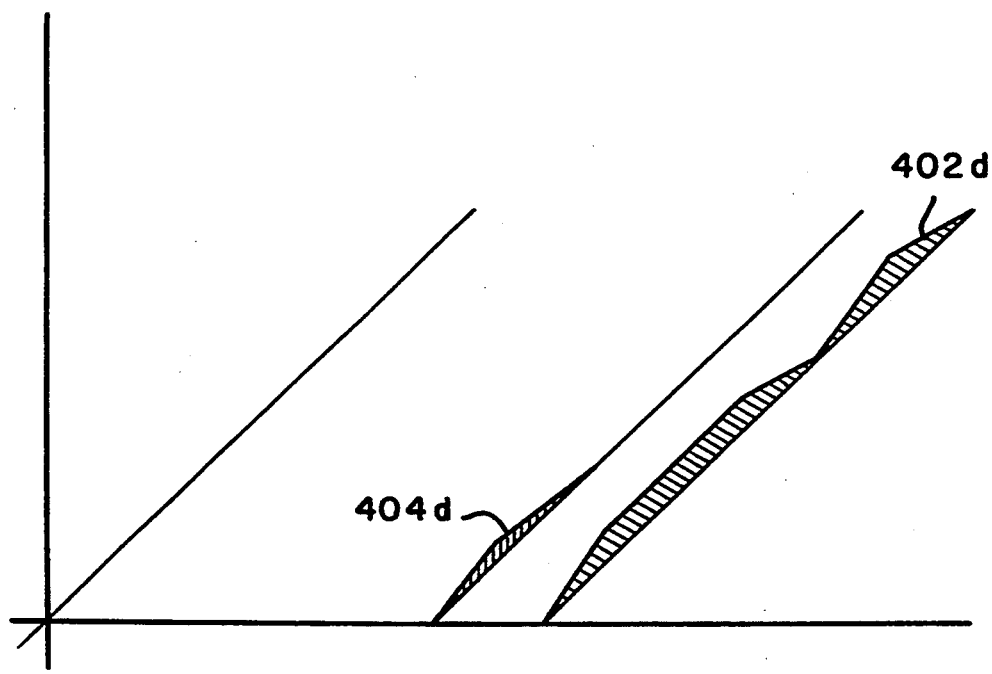
FIG.4-E
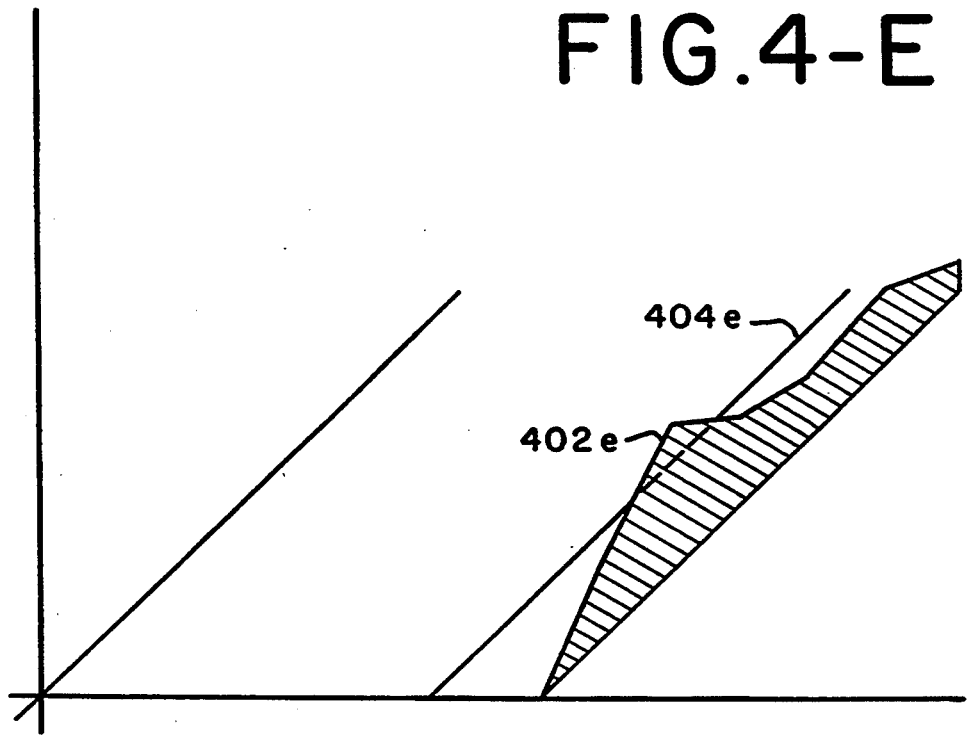

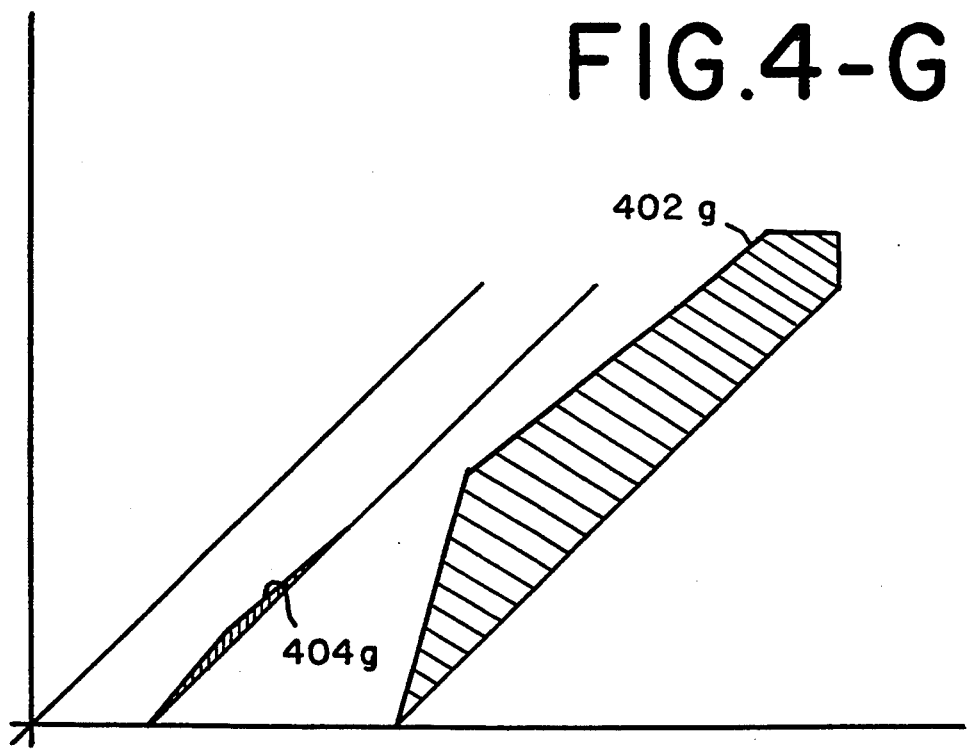
FIG.4-G
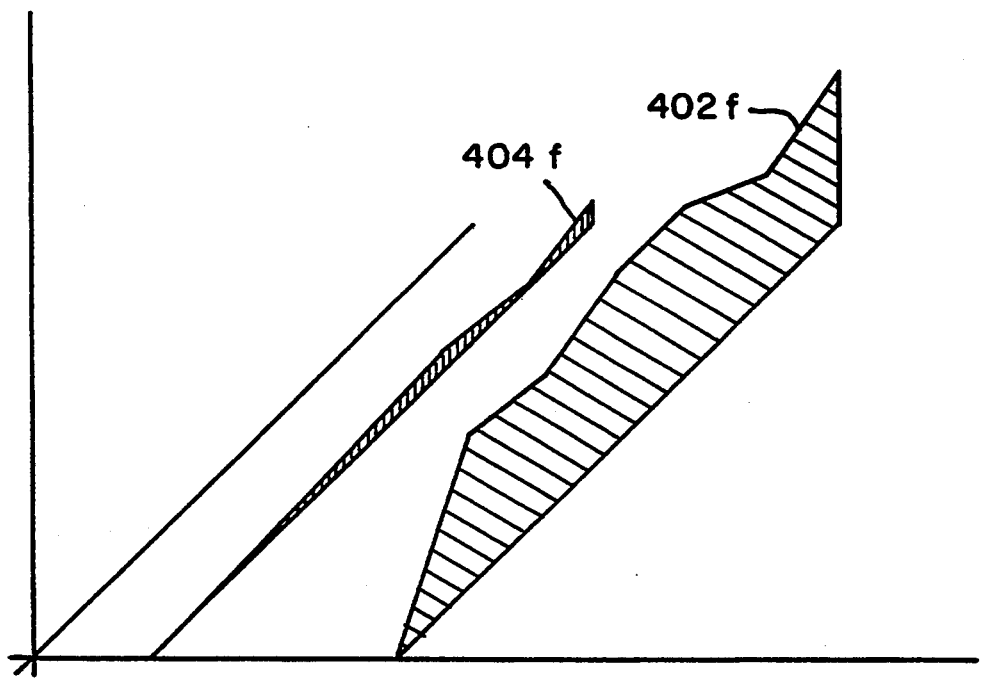
FIG.4-F

FIG.5-A
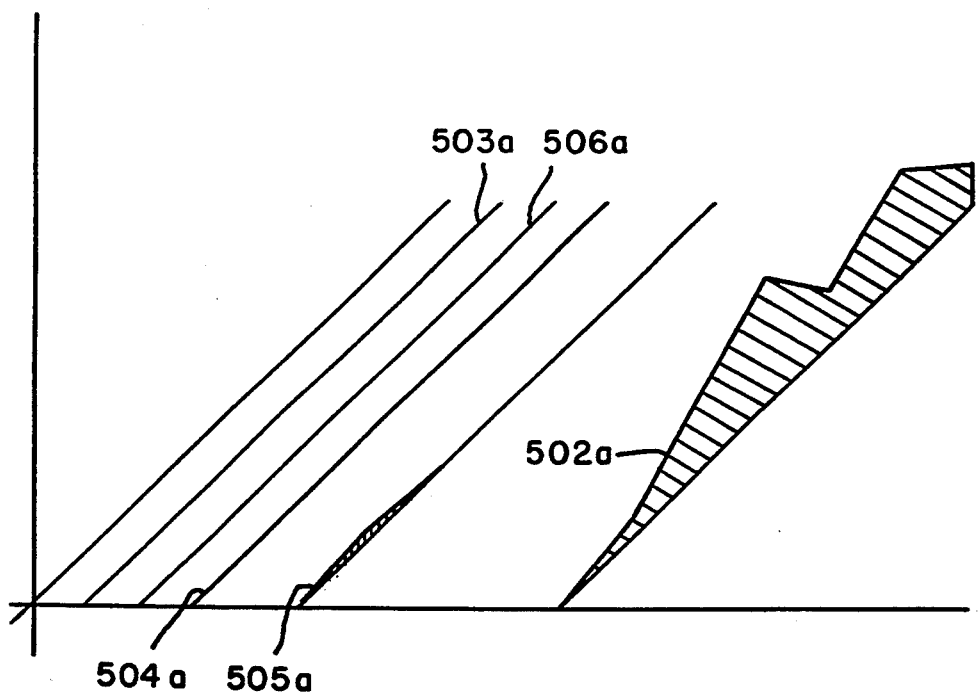
FIG.5-B
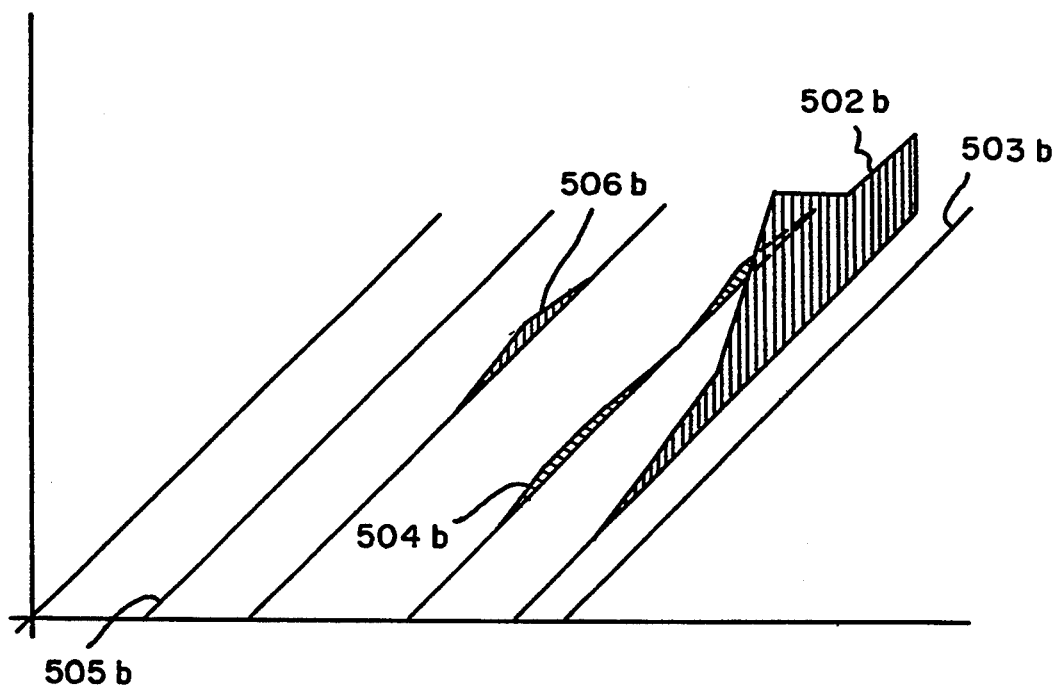

FIG.5-C
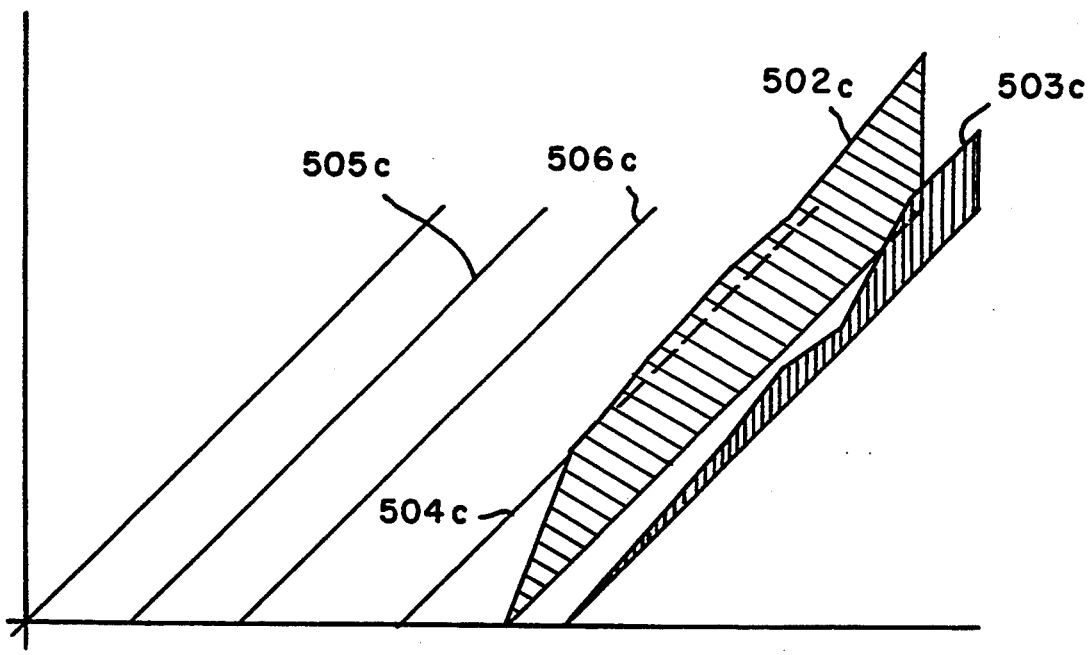
FIG.5-D
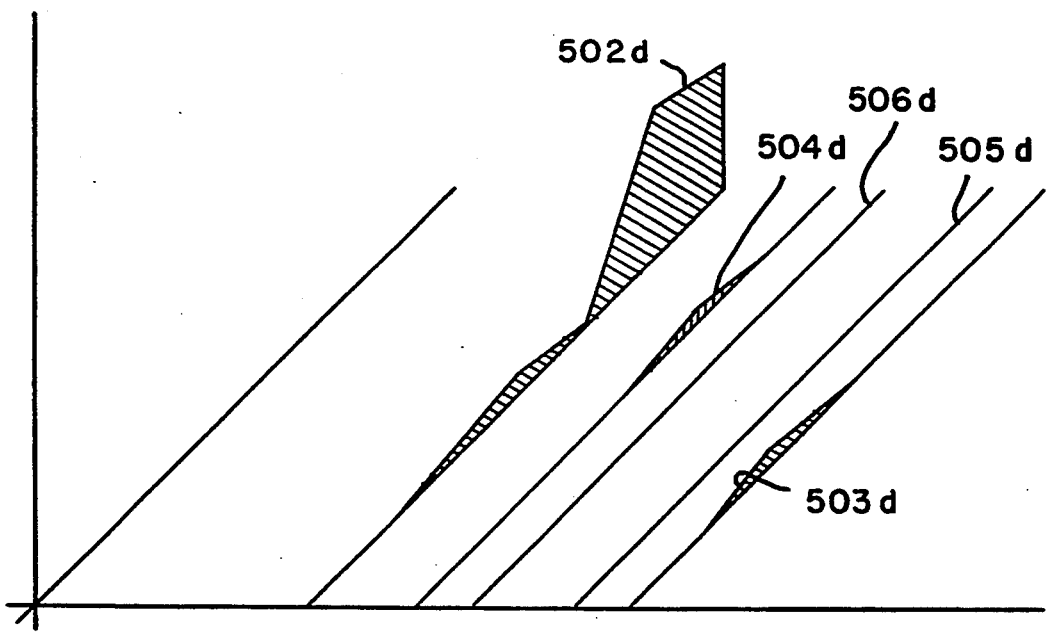

FIG.5-E
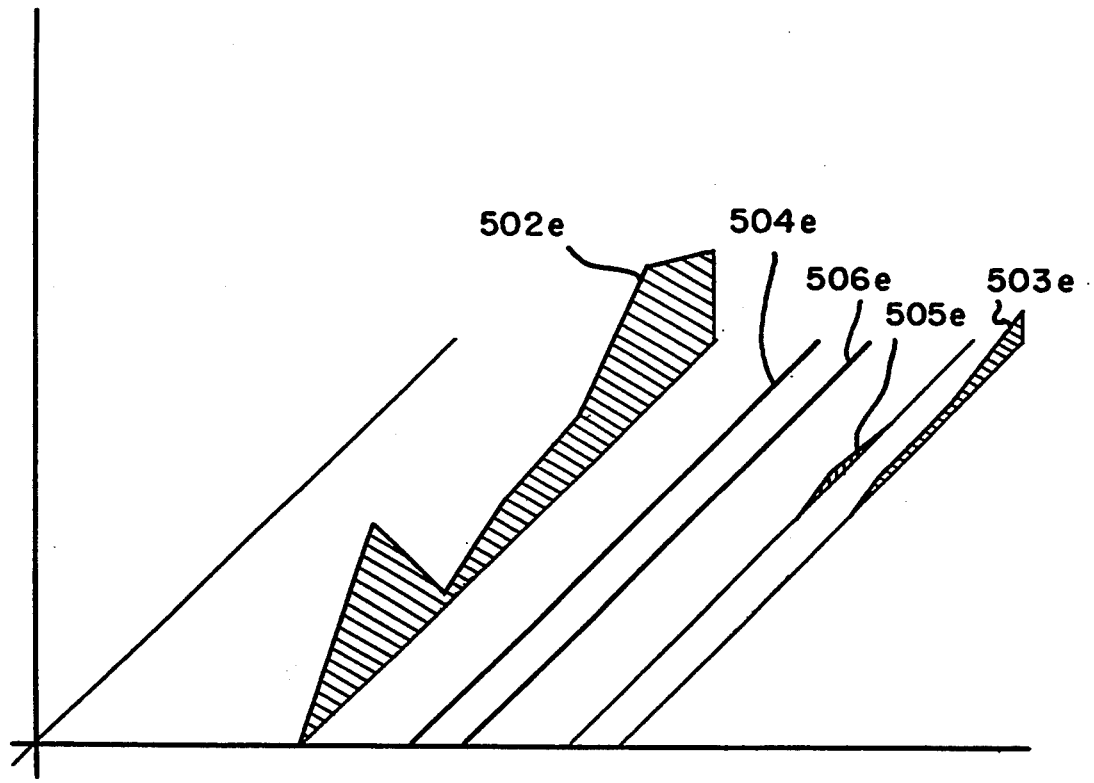

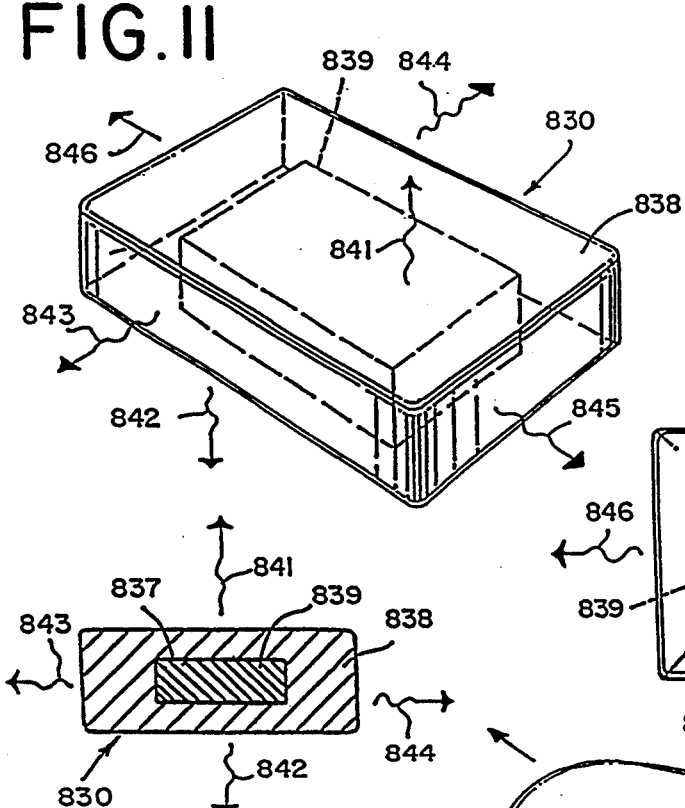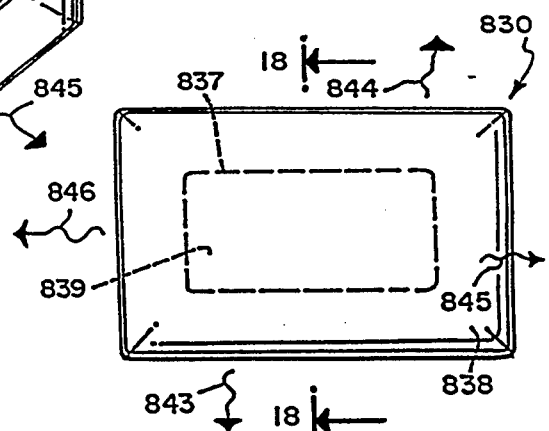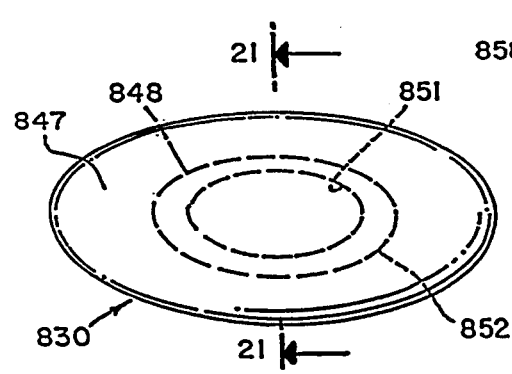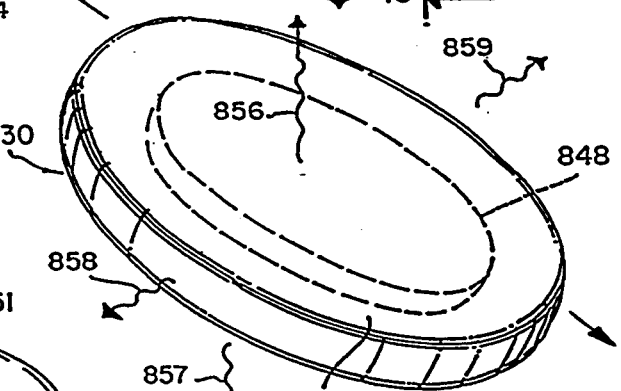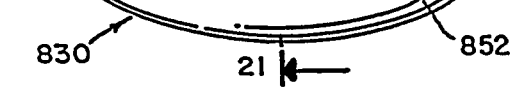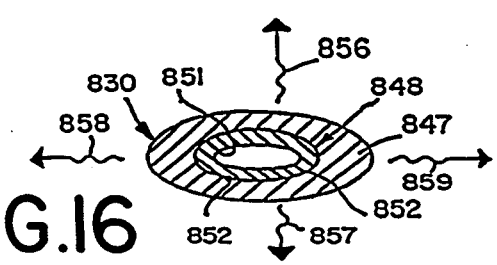

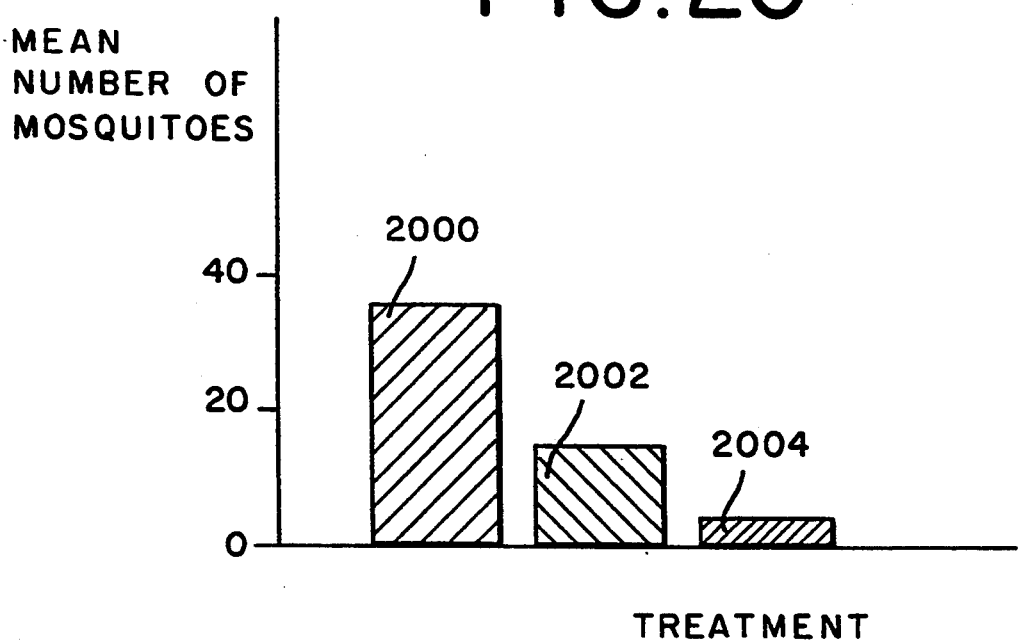

GLC PROFILE FOR EXAMPLE Ⅴ.

GLC PROFILE FOR EXAMPLE Ⅴ, FRACTION 5.

IR SPECTRUM FOR FRACTION 13 OF EXAMPLE V.

GLC PROFILE FOR FRACTION 7 OF EXAMPLE V.

NMR SPECTRUM FOR FRACTION 7 OF EXAMPLE V.

IR SPECTRUM FOR FRACTION 7 OF EXAMPLE V.

GLC PROFILE FOR "INDISAN".

GLC PROFILE FOR EXAMPLE VI, FINAL PRODUCT.

HOUSE FLY, HORN FLY, AND MOSQUITO REPELLENTS AND APPARATUS USEFUL IN TESTING EFFICACY OF SAME

RELATED PATENT APPLICATIONS

This application is Continuation-in-Part application for U.S. patent Ser. No. 982,374 now U.S. Pat. No. 5,281,621 filed on Nov. 25, 1992, which is a continuation of application for U.S. patent Ser. No. 789,695 filed on Nov. 8, 1991, now abandoned, which is a divisional of application for U.S. patent Ser. No. 643,206 filed on Jan. 18, 1991, now U.S. Pat. No. 5,126,369 issued on Jun. 30, 1992. Also related to this case is application for U.S. patent Ser. No. 824,591 filed on Jan. 23, 1992, now U.S. Pat. No. 5,205,065 issued on Apr. 27, 1993, which is a Continuation-in-Part of application for U.S. patent Ser. No. 789,695 filed on Nov. 8, 1991, abandoned, which is divisional of application for U.S. patent Ser. No. 643,106 filed on Jan. 18, 1991, now U.S. Pat. No. 5,126,369.

BACKGROUND OF THE INVENTION

Our invention relates to the use of PAMPLE-FLEUR ® having the structure:

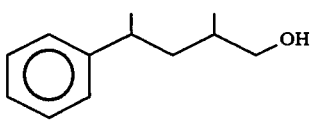

(2,4-dimethyl-4-phenyl-1-butanol), VIOLIFF TM which contains a major quantity of the compound having the structure:

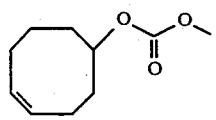

(methyl-4-cyclooctenyl carbonate), ORANGE FLOWER ETHER having the structure:

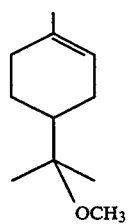

(1-methyl-4(2'-methoxy-2'-propyl)-1-cyclohexene, INDISAN TM containing a major proportion of the compound having the structure:

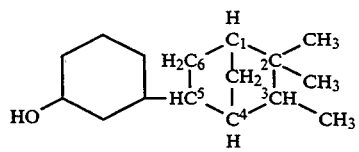

and diethyl phthalate having the structure:

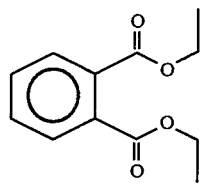

for repelling blood feeding arthropods, species of mosquitoes, house flies and horn flies, as well as apparatus for determining repellency and attractancy of semiochemicals such as the aforementioned materials against and for such blood feeding arthropods.

Ethers, esters and alcohols are known for repelling insects and the prior art contains many references pertaining to same. Thus, the use of the compound having the structure:

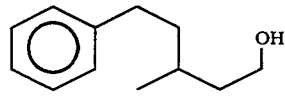

as a repellent against various insect species is disclosed in application for U.S. patent Ser. No. 08/007,287 filed on Jan. 21, 1993, assigned to the assignees of the instant invention.

Nothing in the prior art however sets forth the unexpected, unobvious and advantageous insect repellency properties of the alcohols, ethers and esters of our invention so useful in repelling the species of insects set forth herein.

The prior art is replet with references showing various traps for insects including U.S. Pat. No. 4,759,228 issued on Jul. 26, 1988 and including the above-mentioned application for U.S. patent Ser. No. 08/007,287 filed on Jan. 21, 1993. Other prior art showing such insect traps is:

Griffiths and Bowman, Acarology VI, Volume 2, published by Ellis Horwood Limited 15.5, "Sampling techniques for burrow-dwelling ticks in reference to potential African swine fever virsu vectors", (Butler et al)

Garcia, R., (1962), Ann. Entomol.Soc.Amer., 55 605–606.

Garcia, R., (1965), Amer.J.Trop.Med. Hyg., 14 1090–1093.

Hair, J. A., Hoch, A. L., Barker, R. W., Semtner, P. J., (1972), J. Med. Entomol., 99 153–155.

Holscher, K. H. Gearhart, H. L., Barker, R. W. (1980) Ann.Entomol.Soc.Amer., 73 288–292.

Koch, H. G. & McNew, R. W., (1981), Ann. Entomol.Soc. Amer., 74, 498–500.

Nothing in the prior art sets forth the trap of our invention.

SUMMARY OF THE INVENTION

Our invention is directed to a semiochemical field trap for blood feeding arthropods, which has the capability of causing determination of repellency and attractancy of semiochemicals against and for blood feeding arthropods. The field trap comprises:

(1) An upright vertically disposed first hollow outer housing having substantially rigid arthropod-impermeable first side walls, an upper arthropod-impermeable horizontal surface substantially entirely contiguous with said first side walls, and a substantially entirely open bottom having a substantially horizontal plane substantially perpendicular to the vertical axis of said first hollow outer housing; (for example, such a first hollow outer housing can be a hollow frustum of a cone or a pyramid fabricated from such a material as aluminum);

(2) Located along an axis substantially perpendicular to the horizontal plane of the substantially entirely open bottom of said first outer housing, substantially parallel to the vertical axis of said first hollow housing and within said first hollow housing, a second inner hollow housing having a hollow interior, opposite open upper first and lower second ends, vertically-disposed rigid arthropod-impermeable side walls, and a longitudinal dimension extending between the two ends, said upper first end being at a substantial distance below said upper substantially horizontal surface of said first outer housing (for example, the second inner hollow housing can be an open-ended cylinder fabricated of impermeable tin or aluminum);

(3) Extending outwardly from the substantially vertically disposed side walls of the second inner hollow housing to the side walls of the first hollow outer housing at an angle of from about $-5°$ up to about $-40°$, measured downwardly from the substantially horizontal plane of the open bottom of the first hollow outer housing, substantially rigid rib components (for example, fabricated from steel, stainless steel or iron) which enable the fixed positioning of the inner hollow housing with respect to the positioning of and within said outer hollow housing (the preferred angle being about $-10°$);

(4) Completely encompassingly traversing in a substantially tight fitting manner the area between (i) the first side walls of said first outer hollow housing and (ii) the second side walls of said second inner hollow housing along the directional vectors of said rib components and in a curvilinear plane below and substantially contiguous to said rib components, a continuous substantially macroporous mesh substance having such a mesh size as to be impenetrable by arthropods sought to be entrapped, but pervious to gas and liquid and, in addition, radiation transmittable, and capable of supporting a matrix article containing sustainably releasable semiochemical (for example, nylon mesh having a mesh size in lines per inch of from about 10 up to about 200);

(5) Optionally, at least one semiochemical-containing matrix comprising a porous containment agent (e.g., polyethylene, polypropylene, a polyamid, a polyurethane or the like) containing in the interstices thereof at least one semiochemical sustainably releasable thereform, (e.g., one or more of the ketone, alcohol or schiff base of our invention) located on the upper surface of said macroporous mesh substance (e.g., nylon mesh);

(6) A substantially vertically disposed drive shaft supported for rotary motion about its axis, extending from below and into the hollow interior of the second inner hollow housing along the longitudinal dimension thereof;

(7) Motor means connected to a first lower end of the drive shaft for rotating the drive shaft about its axis;

(8) Air flow creation means (e.g., a propeller) attached to a second upper end of the drive shaft, being of such a design whereby the rotation of the drive shaft directly causes the rotation of the air flow creation means and induces the flow of air from beneath the second inner hollow housing upwardly into the three space within the first outer hollow housing upwardly into the three space within the first outer hollow housing (e.g., the hollow frustum of a cone) between the outer side wall of the second inner hollow housing (e.g., the open ended cylinder) and the inner side wall of the first outer hollow housing (e.g., the hollow frustum of the cone);

(9) Radiation emission means (e.g., an infrared light source or a bright green light source) for emission of radiation of a specific wave length or of a range of wave lengths outwardly from the apparatus located in the vicinity of the lower portion of the second inner hollow housing below the location of the rib components:

(10) Radiation pulsing means connected to said radiation emission means causing said radiation to have a frequency minicking insect wing beat and/or insect visual sensing frequencies;

(11) Power supply means (e.g., flashlight batteries) associated with the trap causing the radiation emission means to generate radiation and energizing the radiation pulsing means and the motor means;

whereby arthropods (e.g., the listed mosquitoes, horn flies and house flies) in the vicinity of the trap are attracted by the pulsed radiation to a location so close to the trap that in the event that an attracting semiochemical in the matrix is detected by the arthropods, the arthropods will enter the air stream created by the air flow creation means and be carried into the 3-space within the first hollow outer housing between the outer side wall of the second inner hollow housing and the inner side wall of the first outer hollow housing. As stated above, it is optional in the operation of the trap to include the semiochemical-containing matrix.

The trap of our invention is intended to test not only semiochemicals (e.g., insect attractants and repellents) and the attractancy or repellency of various types of radiation such as infrared light, but may also be used to test the attractancy or air as well as gases. Thus, the trap of our invention may also include:

(11) A carbon dioxide gas supply means for supplying gaseous carbon dioxide to the proximity of the lower portion of the second inner hollow housing below the location of the rib components simultaneously with the operation of the power supply means. The carbon dioxide itself has the ability to attract various types of insects. It is our intention to cover the trap including and not including the carbon dioxide gas supply means.

Preferably, there should be approximately 0.25 inches $-0.50$ inches clearance between the top of the second inner housing (e.g., cylinder) and the bottom of the upper arthropod-impermeable horizontal surface of the first hollow outer housing. Furthermore, the air flow creation means (e.g., propeller) should preferably protrude 0.125 inches $-0.25$ inches from the bottom of the second inner hollow housing (e.g., open-ended metal cylinder).

It is preferable when using the radiation emission means, to use infrared light. Control experiments are preferably run using carbon dioxide with the use of infrared radiation lights and without the use of infrared radiation lights. However, experiments using the trap may also be carried out with other lights such as bright green lights. In both cases, the radiation emission means utilize the circuit, preferably, of FIG. 5 of U.S. Pat. No. 5,205,065 issued on Apr. 27, 1993, the specification for which is incorporated by reference herein. Other circuits are used when using laser diodes instead of light emitting diodes. An example of the green light being used is one manufactured by the Marktech International Corporation of Menands, N.Y., Catalog Part No. MT300-CUG (T-1.75 water clear ultra-bright green light emitting diode lamp). When using infrared radiation means, it is preferable to utilize a gallium arsenide infrared light emitting diode such as Model MTE 1080 gallium arsenide emitter manufactured by Marktech of 120 Broadway, Menands, N.Y. 12204. When using a laser diode, laser diodes such as those marketed under Catalog Nos. P451 or P452 by the DIGI-KEY ® Corporation of 701 Brooks Avenue South, P.O. Box 677, Thief River Falls, Minn. 56701-0677 are useful and operable. The radiation pulsing means is intended herein to be a flicker fusion frequency generator to present a frequency of from about 50 up to about 400 cycles per second (Herz). Such frequencies are intended to mimic blood feeding arthropod wing beat frequencies and visual sensing frequencies. The radiation pulsing means is intended to cause the firing of, for example, radiation emitting diodes having a range of from about 400 up to about 1000 nm (nanometers).

The radiation pulsing means can be in the form of a direct radiation stroblight such as that illustrated in FIG. 17 of application for U.S. patent Ser. No. 08/007287 filed on Feb. 21, 1993, the specification for which is incorporated by reference herein or it can be in the form of an off-apparatus stroblight unit which causes radiation pulsing to be conveyed through fiber optic strands as set forth, for example, in FIG. 19 of Application for U.S. patent Ser. No. 08/007287 filed on Feb. 21, 1993, the specification for which is incorporated by reference herein.

In any event, radiation pulsing means which can be used in the practice of our invention are set forth in the following publications:
  (i) published Canadian Patent Application 2,040,615 published on Oct. 17, 1992 (title: "Cel-Alert" An Easy To-Use Emergency Strobe-Light Road Safety Device";
  (ii) the Stroboscope/Tachometer marketed by the Edmund Scientific Company of Barrington, N.J.;
  (iii) the "Realistic Wide Angle Strobe Light" Catalog No. 42-3009A marketed by the Radio Shack Division of Tandy Corporation of Ft. Worth, Tex.;
  (iv) the Enerlite Personal Strobe, Catalog No. 61-2506 marketed by the Radio Shack Division of Tandy Corporation of Ft. Worth, Tex.

Other light emitting diodes that are useful in the practice of our invention are, for example, those set forth in Canadian Published Patent Application 2,065,577 published on Oct. 17, 1992 entitled "Encapsulated Light Emitting Diode And Method For Encapsulation".

When preparing the semiochemical matrix which is preferably a block, 10 microliters of test material, e.g., at least one of the alcohols, esters or ether used in our invention are soaked into a 9 mm×9 mm×9 mm block. The carbon dioxide supply source is most conveniently dry ice placed in a "zippered" bag (with a tygon tubing outlet). The dry ice is placed in a zippered bag and the bag is then placed in an insulated ice chest. Preferably between 4 and 5 kilograms of dry ice is used, preferably in the form of pellets or blocks.

On placing the trap in the test area, the motor means is engaged with the power supply means, preferably simultaneously with the engagement of the radiation means and radiation pulsing means with the power supply means. Thus, at the instant that the trap is commenced to be in use, the air flow or carbon dioxide flow creation means (e.g., the propeller) begins its rotation simultaneously with the radiation means and radiation pulsing means being energized and with the motor means being energized. Thus, arthropods, e.g., mosquitoes, house flies, and horn flies as set forth, supra, in the vicinity of the trap are attracted by the pulsing radiation to a location so close to the trap that in the event that an attracting semiochemical in the matrix is detected by the arthropods, the arthropods will enter the air or carbon dioxide stream created by the air flow creation means, e.g., propeller and be carried into the 3-space within the first hollow outer housing between the outer side wall of the second inner hollow housing and the inner side wall of the first outer hollow housing. Once within the trap the arthropods will not escape in view of the fact that they are in the vicinity of the carbon dioxide being emitted by the carbon dioxide supply source and they are in the vicinity of the pulsing radiation emitted by the pulsing radiation emission means and are attracted thereto. Furthermore, the rotation of the air flow creation means prevents the arthropods from leaving the 3-space within the first hollow outer housing where they are trapped. The traps are usually run for a period of from about 36 hours up to about 40 hours. They are set up in usually four rows of four, approximately 60 feet apart.

Preferably, the mesh size of the nylon used for the continuous substantially macroporous mesh substance of the trap should range from about 10 up to about 200 lines per inch and thus, for example, may be 20/6 T-66 textured nylon or 70/32 polyester (e.g., a polymer of phthalic anhydride and ethylene glycol).

More specifically, our invention is directed to a method for repelling at least one of the insect species:
  (a) *Musca domestica* L.(Diptera:Muscidae);
  (b) *Aedes aegypti;*
  (c) *Aedes albopictus;*
  (d) Anopheles spp.;
  (e) *Coquillettidia perturbans;*
  (f) Culiseta Spp.;
  (g) Culex spp.;
  (h) Psorophora spp.;
  (i) Culicoides spp.;
  (j) Lutzomyia spp.;
  (k) Aedes spp.;
  (l) *Culex nigripalpus;*
  (m) *Aedes atlanticus;*
  (n) *Culex salinarius;*
  (o) *Aedes vexans;*
  (p) Simuliidae spp.;
  (q) *Psorohora ferox;*
  (r) *Aedes infirmatus;*
  (s) *Drosophila melanogaster;*
  (t) Coccinellidae;
  (u) *Anopheles crucian;*
  (v) *Psorophora columbiae;* and
  (w) *Haemotobia irritans* (L.)
for a finite period of time from a three dimensional space comprising the step of exposing said three dimensional space inhabited by:
  (a) *Musca domestica* L.(Diptera:Muscidae);
  (b) *Aedes aegypti;*
  (c) *Aedes albopictus;*
  (d) Anopheles spp.;
  (e) *Coquillettidia perturbans;*
  (f) Cullseta spp.;

(g) *Culex* spp.;
(h) *Psorophora* spp.;
(i) *Culicoides* spp.;
(j) *Lutzomyia* spp.;
(k) *Aedes* spp.;
(l) *Culex nigripalpus;*
(m) *Aedes atlanticus;*
(n) *Culex salinarius;*
(o) *Aedes vexans;*
(p) *Simuliidae* spp,;
(q) *Psoroforia ferox;*
(r) *Aedes infirmatus;*
(s) *Drosophila melanogaster;*
(t) *Coccinellidae;*
(u) *Anopheles crucian;*
(v) *Psorophora columbiae;* and
(w) *Haemotobia irritans* (L.)

to a composition of matter which is at least one of the esters, alcohols or ether-containing composition of matter, to wit:

(1) PAMPLEFLEUR ® having the structure:

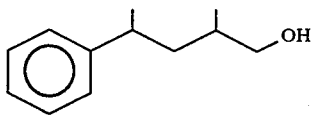

(2,4-dimethyl-4-phenyl-1-butanol) prepared according to Example III, columns 20, 21 and 22 of U.S. Pat. No. 4,610,812 issued on Sep. 9, 1986, the specification for which is incorporated by reference herein;

(2) VIOLIFF ™ containing a major amount of the compound having the structure:

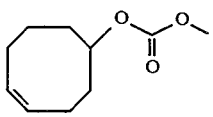

and a minor amount of the compound having the structure:

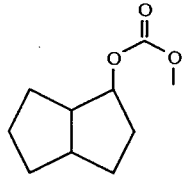

prepared according to the process of Example II (bulked distillation Fractions 7–14) of U.S. Pat. No. 4,452,730 issued on Jun. 5, 1984, the specification for which is incorporated by reference herein; produced according to the process of
(i) reacting 1,5-cyclooctadiene with formic acid to form a mixture of formates containing a major quantity of 4-cyclooctenyl formates; and
(ii) reacting the resulting mixture of formates with dimethyl carbonate in the presence of an alkali metal methoxide to form a mixture of methyl carbonate containing a major quantity of 4-cyclooctenyl methyl carbonate;

(3) ORANGE FLOWER ETHER having the structure:

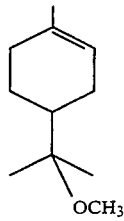

(1-methyl-4(2'-methoxy-2'-propyl)-1-cyclohexene;

(4) A mixture of compounds containing a major proportion of the compound having the structure:

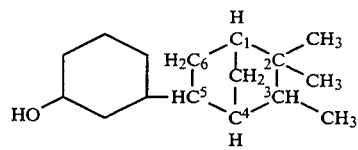

(for example, INDISAN ™ or SANDIFF ™ (trademark of International Flavors & Fragrances Inc.)) prepared by:
(i) reacting catechol or quiacol with camphene in the presence of a Friedel-Crafts Catalyst to form an alkylation product;
(ii) treating the alkylation product with hydrogen to form a dioxy intermediate; and then
(iii) treating the dioxy intermediate with hydrogen to form a meta-(isocamphyl-5) cyclohexanyl containing mixture (for example, prepared according to the process of Example XIII of U.S. Pat. No. 4,014,944 issued on Mar. 29, 1977 the specification for which is incorporated by reference herein); and (5) Diethyl phthalate having the structure:

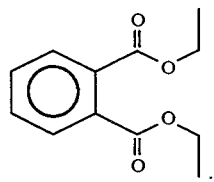

Another aspect of our invention relates to the formation of the insect repelling articles, that is, the articles containing at least one of the alcohols, esters and/or ether useful for the repelling of the insect species:
(a) *Musca domestica* L.(Diptera:Muscidae);
(b) *Aedes aegypti;*
(c) *Aedes albopictus;*
(d) *Anopheles* spp.;
(e) *Coquillettidia perturbans;*
(f) *Culiseta* spp.;
(g) *Culex* spp.;
(h) *Psorophora* spp.;
(i) *Culicoides* spp.; and/or
(j) *Lutzomyia* spp.;
(k) *Aedes* spp.;
(l) *Culex nigripalpus;*
(m) *Aedes atlanticus;*
(n) *Culex salinarius;*
(o) *Aedes vexans;*

(p) *Simuliidae* spp.;
(q) *Psorophora ferox;*
(r) *Aedes infirmatus;*
(s) *Drosophila melanogaster;*
(t) *Coccinellidae;*
(u) *Anopheles crucian;*
(v) *Psorophora columbiae;* and
(w) *Haemotobia irritans* (L.)

in combination with compatible polymers, e.g., high density polyethylene or low density polyethylene. Thus, one aspect of our invention provides a process for forming semiochemical-containing polymeric particles such as foam polymeric pellets which include a relatively high concentration of at least one of the alcohols, esters and/or ether useful in our invention.

Thus, one aspect of our invention relates to the formation of semiochemical polymeric pellets by means of introduction into a single screw or twin screw extruder of, in series, a thermoplastic polymer followed by a semiochemical which is compatible with the thermoplastic polymer, in turn (optionally) followed by introduction of a gaseous blowing agent or blowing agent which will produce a gas which is inert to the polymer and to the alcohols, esters and ether semiochemical previously introduced into the extruder.

The advantages of using a foamed polymeric particle are multiple, to wit: improved handling, greater retention of the semiochemical, that is, at least one of the alcohols, esters or ether when not in use; greater length of time during which the release of the semiochemical from the polymer is at "steady state" or "zero order".

The nature of the extruder utilized in the process of our invention to form the polymeric semiochemical-containing polymer particles of our invention may be either single screw or double screw. Thus, the types of extruder that can be used are disclosed at pages 246–257 and 332–349 of the Modern Plastics Encyclopedia, 1982–1983, published by the McGraw-Hill Published Company. More specifically, examples of extruders which are usable in carrying out one of the processes of our invention (with modification for introduction of the semiochemical) downstream from the introduction of the polymer and with further modification that the gaseous blowing agent is introduced still further downstream from the point of introduction of the semiochemical, e.g., at least one of the alcohols, esters and/or ether of our invention are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kan. 67277;
3. Modified Sterling Model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc.1 of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactued by the Werner & Pfleiderer Corporation of 6763 East Crescent Avenue, Ramsey, N.J. 07446;
7. The Farrel Extruder manufactured by Farrel Connecticut Division, Emhart Machinery Group, Ansonia, Conn. 06401;
8. The MpC/V Baker Perkins Twin Screw Extruder manufactured by the Baker Perkins Inc. Chemical Machinery Division of Saginaw, Mich. 48601; and
9. The Berstorff single screw, twin screw, or foam extrusion equipment manufactured by Berstorff Corporation, P.O. Box 240357, 8200-A Arrowridge Boulevard, Charlotte, N.C. 28224.

In producing the semiochemical (e.g., alcohols, esters and/or ether) polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed copolymer of ethylene and vinyl acetate. Prefered copolymers are polyethylene-vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. dupont de Nemours Company under the tradename "ELYAX®" and by the Arco Polymer Division under the trademark "DYLAND®" and by the Exxon Corporation of Linden, New Jersey under the trademark "DEXXON®". Ethylene/ethyl acrylate co-polymers are marketed by Union Carbide Corporation under the tradename "EEA RESINS®".

The polymer is added to the single screw or twin screw extruder at a feed rate in the range of from about 80 up to about 300 pounds per hour while maintaining the temperature of the screw extuder between about 160° and about 240° C. If the polymer or co-polymer powder is added to the extruder at a reference "barrel segment", then at least one of the alcohols, esters or ether useful in our invention is added to the extruder under pressure downstream from the addition point of the polymer at one or more of "barrel segments" S-2, S-3, S-4, S-5, S-6, S-7, S-8 or S-9 (referring to FIG. 6 briefly described, infra, and described in detail, infra).

The concentration of at least one of the alcohols, esters or ether in the semiochemical-containing resin can vary from small but effective amounts on the order of about 1% of the weight of the resin body up to about 45% by weight of the resin body. In general it is preferred to use between about 5% up to about 30% based on the weight of the resin body of at least one of the esters, alcohols or ethers useful in our invention. This is an optimum amount balancing the proportion of at least one of the esters, alcohols or ether useful in our invention against the time period over which the article omits at least one of the esters, alcohols or ether useful in our invention and against the tendency of at least one of the alcohols, esters or ether to "oil out". This "oiling out" is specifically avoided as a result of the use of the foaming agent discussed, infra.

Various polymers are useful in the practice of our invention. Specific examples of polymers useful in the practice of our invention are as follows:

(a) DYLAN ® brand of low density polyethylene DYLAN ® is a trademark owned by the Atlantic Richfield Company of Los Angeles, Calif.;

(b) DYLITE ® of expandable polystyrene compositions. DYLITE is a trademark of the Atlantic Richfield Company of Los Angeles, Calif.;

(c) SUPER DYLAN ® is a high density polyethylene. SUPER DYLAN ® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/alpha-olefin as exemplified and disclosed U.S. Pat. No. 4,369,291, the specification for which is incorporated by reference herein;

(g) Poly-alpha-olefins as exemplified in Canadian Letters Patent No. 1,137,069 issued on Dec. 7, 1982;

(h) Polymeric compositions as disclosed in Canadian Letters Patent No. 1,137,068 issued on Dec. 7, 1982;

(i) Poly-alpha-olefins disclosed in Canadian Letters Patent No. 1,137,067;

(j) Polyolefins described in Canadian Letters Patent No. 1,137,066;

(k) Polyethylene oxides as disclosed in Canadian Letters Patent No. 1,137,065 issued on Dec. 7, 1982;

(l) Olefin polymers and co-polymers as disclosed in Canadian Letters Patent No. 1,139,737; Canadian Patent No. 1,139,737 was issued on Jan. 18, 1983;

(m) Polyolefins disclosed in Canadian Letters Patent No. 1,139,738; Canadian Patent No. 1,139,738 was issued on Jan. 18, 1983;

(n) Chlorinated PYC as disclosed in Polymer 1982, 23 (7, Suppl.), 1051–6 abstracted at Chem. Abstracts Volume 97:145570y, 1982;

(o) Polyepsilon caprolactone co-polymers made by means of alcohol initiated polymerization as disclosed in J.Polym.Sci.Polym.Chem. Ed., 1982, 20(2), pages 319–26, abstracted at Chem. Abstracts Volume 96:123625x, 1982;

(p) Styrene acrylonitrile co-polymers as disclosed in Diss. Abstracts, Int. B, 1982, 42(8), 3346 and abstracted at Chem. Abstracts Volume 96:143750n (1982);

(q) Co-polymers of epsilon caprolactone with 1,4-butane diol as disclosed at Kaucho Rezine, 1982, (2), 8–9, abstracted at Chem. Abstracts Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, J.Polym.Sci.Polym., Phys.Ed, 1982, 20(2), 191–203;

(t) Plasticized polyepsilon caprolactone co-polymers containing dimethyl phthalate plasticizers as set forth in Japanese Patent No. J81/147844, abstracted at Chem. Abstracts Volume 96:69984y (1982);

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the specification for which is incorporated by reference herein.

Downstream from the addition point of at least one of the esters, alcohols or ether, optionally, the gaseous or liquid, containing blowing agent may be added (e.g., at barrel segments S-5, S-6, S-7, S-8, S-9 or S-10 of FIG. 6) using the polymer addition barrel segment as a reference barrel segmen "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. This gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed ester, alcohol or ether-containing particle.

The feed rate range of the of the ester, alcohol or ether may be between about 0.5% up to about 45% by weight of the polymer.

The die of the extruder may create rod, sheet, film or ribbon. The resulting product may then, if desired, be pelletized to form alcohol, ester or ether (e.g., the ORANGE FLOWER ETHER having the structure:

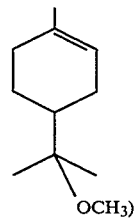

-containing polymer particles or the ribbon may be used "as-is" as an alcohol, ester or ether containing polymeric article of manufacture itself.

In addition to the optional gaseous blowing agents (which are necessarily "inert" gases), blowing agents may be added at the same point on the extruder which will create gaseous voids in the alcohol, ester or ether-containing polymer articles of our invention and these "blowing agents" are well known to one having ordinary skill in the art.

Examples of such non-gaseous containing materials which yield gases on admixture with the polymer in the extruder but which are still inert to the insect repellent are as follows:
  (i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated hereby by reference herein;
  (ii) Ordinarily liquid material such as n-pentane, isopentans, cyclopentane, texans and petroleum ether fractions or halogen hydrocarbons such as $CFC_3$, $CF_2Cl_2$, $Ch_3Cl$, $CH_2Cl_2$ separately or in admixture with one another as set forth in U.S. Pat. No. 3,758,425, column 4, lines 1–5, the specification for which is incorporated hereby by reference herein;
  (iii) Dichlorohetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specification for which is incorporated hereby by reference; and
  (iv) Azo bis(formamide)l diazoaminobenzene; N,N'-dinitrosopentamethylene tetramine; N,N'-dimethyl-N,N'-dinitrosoterephthalamide; p,p'-oxy-bis(-benzene sulfonyl semicarbazide); azo bis-(isobutyronitrile); p,p'-oxybis(benzene sulfonyl hydrazide); p,p'-diphenyl-bis (sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated hereby by reference herein.

The resulting extruded (and if desired, pelletized) material may then be, for example, be injection molded to form a useful article such injection molding can be carried out in accordance with the procedure as set forth in U.S. Pat. No. 3,268,636 issued on Aug. 23, 1966, the specification for which is incorporated hereby by reference herein.

In addition, our invention relates to candle body materials which on use are both insect repellent and perfuming and which contain of at least one of the esters alcohols and/or ether of our invention (e.g., the PAMPLEFLEUR ® having the structure:

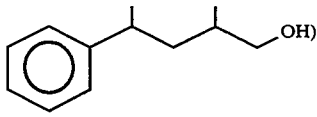

in order to repel at least one of the insect species:
  (a) *Musca domestica* L.(Diptera:Muscidae);
  (b) *Aedes aegypti;*
  (c) *Aedes albopictus;*
  (d) Anopheles spp.;
  (e) *Coquillettidia perturbans;*
  (f) Culiseta spp.;
  (g) Culex spp.;
  (h) Psorophora spp.;
  (i) Culicoides spp.; and/or
  (j) Lutzomyia spp.;
  (k) Aedes spp.;
  (l) *Culex nigripalpus;*
  (m) *Aedes atlanticus;*
  (n) *Culex salinarius;*
  (o) *Aedes vexans;*
  (p) Simuliidae spp.;
  (q) *Psorophora ferox;*
  (r) *Aedes infirmatus;*
  (s) *Drosophila melanogaster;*
  (t) Coccinellidae;
  (u) *Anopheles crucian;*
  (v) *Psorophora columbiae;* and
  (w) *Haemotobia irritans* (L.)

The insect repellent-perfume compositions which form part of the candle body materials are within the following specifications:
  (I) from 5 up to 100% by weight of an efficacious perfume/insect repellent composition consisting essentially of at least one of the alcohols, esters and/or ether useful in our invention, e.g., a mixture of PAMPLEFLEUR ® having the structure:

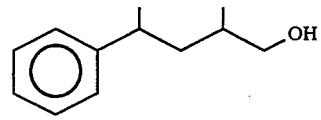

and VIOLIFF TM having a major proportion of the compound having the structure:

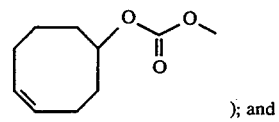

(II) from 0 up to 95% of a standard perfuming substance (not necessarily insect repellent) which may be one a combination of the following materials:
    the methyl ester of 2,5-dihydroxy-4-5-dimethyl benzoic acid;
    dihydro myrcenol;
    oakmoss absolute;
    benzyl acetate;
    geraniol;
    isobornyl acetate;
    citronelly acetate;
    para-t-butyl phenyl isovaleraldehyde
    benzyl salicylate;
    hexyl cinnamic aidehyde
    geranonitrile;
    patchouli oil;
    alpha-terpineol;
    tetrahydromuguol;
    phenyl ethyl alcohol;
    cedrenal;
    cinnamyl acetate;
    benzyl benzoate;
    L-Citronellal;
    nerol;
    geranyl formate;
    geranyl acetate;
    eugenol;
    alpha Farnesene;
    beta Farnesene;
    citral;
    n-Nonanal;
    n-Octanal; and
    trans, trans delta-damascone The foregoing formulae may require a solubilizing agent, e.g., the methyl ester of dihydroabietic acid (commerical name: HERCOLYN D ®, benzyl benzoate, isopropyl myristate and/or $C_{12}$–$C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;
(ii) an alkanol amide or alkanol amine; and
(iii) a stearic acid compound.

The weight ratio of the candle body: ester, alcohol or ether (e.g., ORANGE FLOWER ETHER having the structure:

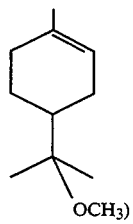

perfumant substance of our invention may vary from about 0.8% up to about 10% with a range of from about 0.8% up to about 2.0% being preferred when no non-insect repelling perfume oil is used in conjunction with the alcohol, ester and/or ether composition of matter useful in our invention; and with a range of from about 1.5% up to about 10% by weight of the overall composition being preferred when a non-insect repelling perfume oil is used in conjunction with the ester, alcohol and/or ether useful in our invention.

Specifically, the polyamide may be a "VERSAMID ®" resin which is a thermoplastic condensation product of polymerized linoleic acid with various polyamine compounds such as ethylene diamine, ethylene triamine and the like. Specific "VERSAMID ®" compounds are "VERSAMID ®"900, "VERSAMID ®"930, "VERSAMID ®"940, "VERSAMID ®"948, "VERSAMID ®"950 and "VERSAMID ®"1635. These compounds are products of the Henkel Chemical Corporation of Minneapolis, Minn. and "VERSAMID ®" is a trademark of Henkel Chemical Corporation of Minneapolis, Minn.

Another substance required in the clear candle composition consists of about 20–55% by weight of an alkanol amine or alknaol amide prepared by the reaction of a fatty acid ester and amine whereby the ester and the amine are in substantially equal proportions, for example, compounds such as Barlol 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection it is possible to use up to about 10% by weight of perfumant/insect repellent if part of the formula is replaced by the material "Nevex 100", a product which is a coumarin-indene copolymer resin of very little unsaturation, manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperature. Such a gel is disclosed in U.S. Pat. No. 3,645,705 issued on Feb. 29, 1972, the disclosure of which is incorporated by reference herein. Such compositions of matter include:

(a) from about 35% up to about 85% by weight of an oil which is normally liquid at room temperature chosen from the group consisting of light mineral oil and natural oils having iodine values substantially within the range of 40–135;
(b) from about 7% up to about 40% by weight of a long chain polyamide having a molecular weight substantially within the range of 6000–9000 and a softening point substantially within the range of 18° C.–48° C.; and
(c) from about 7% to about 30% of an alcohol selected from the group consisting of 8 to 12 carbon primary alcohols.

Such composition may additionally include from about 1% up to about 15% of a methyl ester; up to about 5% by weight of stearic acid and up to about 5% by weight of an oxidation inhibiting agent and up to about 5% by weight of an acid selected from the group consisting of dimer and trimer acids.

FIG. 1 is a cut-away perspective view of the semiochemical field trap for blood feeding arthropods of our invention showing blood feeding arthropods inside the trap being attracted to semiochemical-containing matrices comprising a porous containment agent containing in the interstices thereof at least one semiochemical sustainably releaseable therefrom.

FIG. 2 is a schematic diagram (blown up for illustration purposes) showing laboratory olfactometer apparatus in perspective view useful in ascertaining the efficacy of the esters, alcohols and ether composition of our invention useful as repellents for house flies (*Musca domestica* L.(Diptera:Muscidae)) and mosquitoes (*Aedes aegypti*) indicating in schematic block flow diagram form the utilization of computer assisted efficacy measuring apparatus.

FIG. 2A is a detailed section of the apparatus of FIG. 2 showing a specific landing site on which an insect lands if attracted by, for example, an ester, alcohol or ether-containing composition useful in our invention (e.g., the ORANGE FLOWER ETHER having the structure:

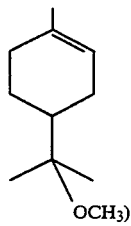

OCH₃)

or does not land if repelled by the alcohol, ester or ether-containing composition useful in our invention.

FIG. 3A is a bar graph showing the attractancy of air versus the repellency of diethylphthalate using the apparatus of FIG. 2 with a mean one hour feeding contact. The number of feeding contacts for mosquitoes (*Aedes aegypti*) is shown on the "y" axis and the given treatment is shown on the "x" axis.

FIG. 3B is a bar graph similar to that of FIG. 3A except that the feeding contact is a mean 2-6 hour contact.

Figure 1:
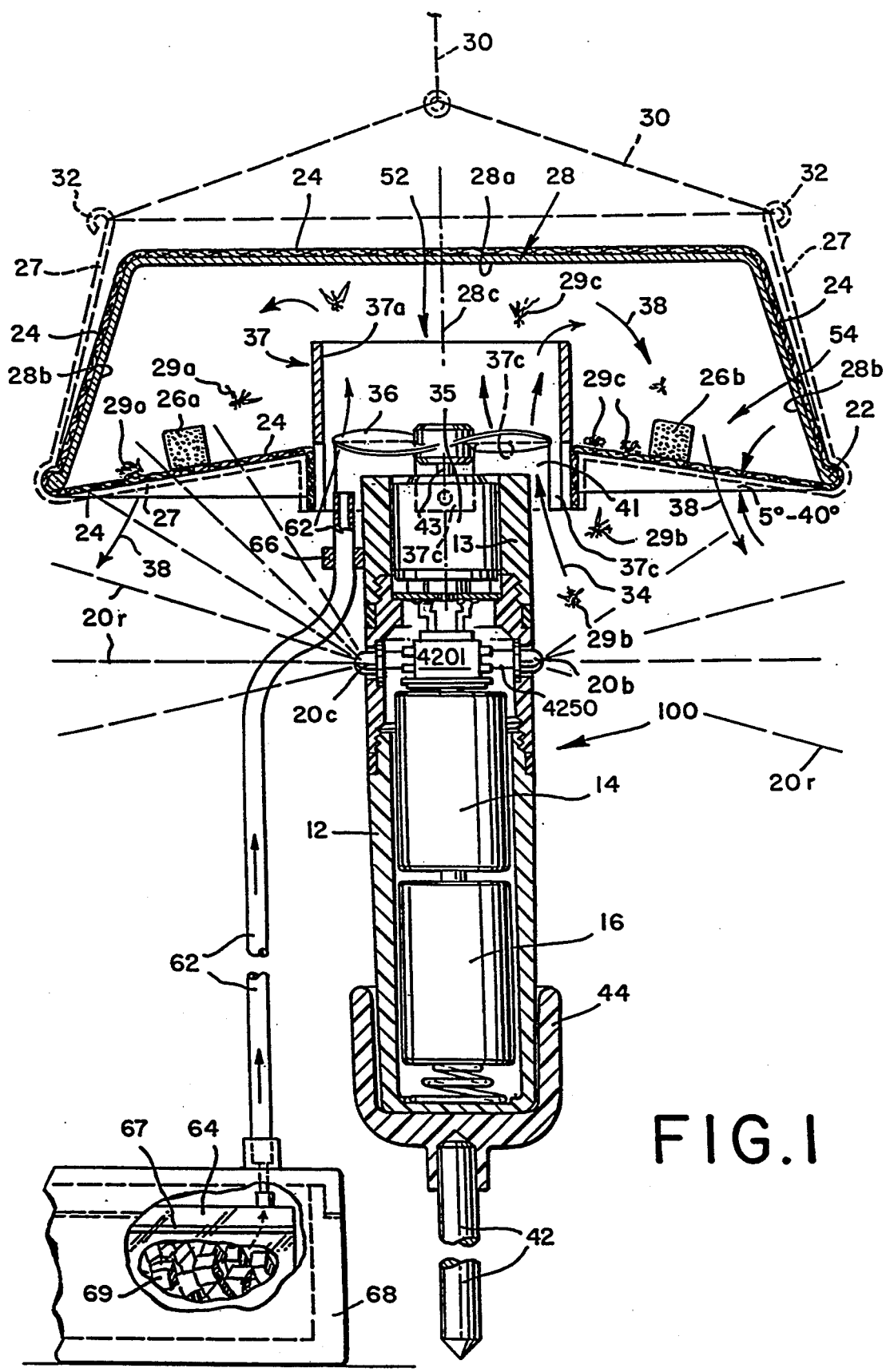

FIG. 4A is a series of graphs depicting in three dimensions (in the rectangular mode for the "x" and "y" axes) showing the repellency of INDISAN TM as well as the attractiveness of air. The graphs are based on experiments run for a total of one hour with six intervals of 10 minutes each. The results are tabulated in Table I, infra. This series of graphs is for the attractiveness or repellency against house flies (*Musca domestica* L.(Diptera:Muscidae)).

FIG. 4B is a series of graphs depicted in three dimensions (in a rectangular mode for the "x" and "y" axes) showing the repellency of INDISAN TM as well as the attractiveness of air. The graphs are based on experiments run for a total of one hour with six intervals of 10 minutes each. The results are tabulated in Table II, infra. This series of graphs is for the attractiveness or repellency as against horn flies (*Haemotobia irritans* (L.)).

FIG. 4C is a series of graphs depicted in three dimensions (in a rectangular mode for the "x" and "y" axes) showing the repellency of INDISAN TM as well as the attractiveness of air. The graphs are based on experiments run for a total of one hour with six intervals of 10 minutes each. The results are tabulated in Table III, infra. This series of graphs is for the attractiveness or repellency as against mosquitoes (*Aedes aegypti*).

FIG. 4D is a series of graphs depicted in three dimensions (in a rectangular mode for the "x" and "y" axes) showing the repellency of INDISAN TM as well as the attractiveness of air. The graphs are based on experiments run for a total of twelve hours with six intervals of two hours each. The results are tabulated in Table IV, infra. This series of graphs is for the attractiveness or repellency as against mosquitoes (*Aedes aegypti*).

FIG. 4E is a series of graphs depicted in three dimensions (in a rectangular mode for the "x" and "y" axes) showing the repellency of INDISAN TM as well as the attractiveness of air. The graphs are based on experiments run for a total of one hour with six intervals of ten minutes each. The results are tabulated in Table V, infra. This series of graphs is for the attractiveness or repellency as against mosquitoes (*Aedes aegypti*).

FIG. 4F is a series of graphs depicted in three dimensions (in a rectangular mode for the "x" and "y" axes) showing the repellency of INDISAN TM as well as the attractiveness of air. The graphs are based on experiments run for a total of one hour with six intervals of ten minutes each. The results are tabulated in Table VI, infra. This series of graphs is for the attractiveness or repellency as against mosquitoes (*Aedes aegypti*).

FIG. 4G is a series of graphs depicted in three dimensions (in a rectangular mode for the "x" and "y" axes) showing the repellency of INDISAN TM as well as the attractiveness of air. The graphs are based on experiments run for a total of twelve hours with six intervals of two hours each. The results are tabulated in Table VII, infra. This series of graphs is for the attractiveness or repellency as against mosquitoes (*Aedes aegypti*).

FIG. 5A is a series of graphs depicted in three dimensions (in a rectangular mode for the "x" and "y" axes) showing the relative repellency of ORANGE FLOWER ETHER (having the structure:

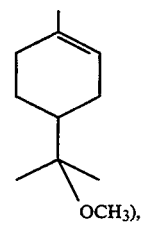

OCH₃),

PAMPLEFLEUR ® having the structure:

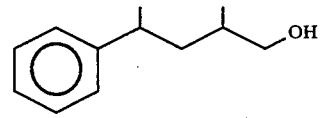

and VIOLIFF TM having as its major ingredient the compound having the structure:

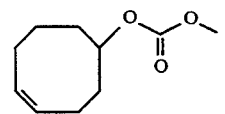

as well as the attractiveness of air. The graphs are based on experiments run for a total of one hour with six intervals of ten minutes each. The results are tabulated in Table VIII, infra. This series of graphs is for the attractiveness or repellency as against mosquitoes (*Aedes aegypti*).

FIG. 5B is a series of graphs depicted in three dimensions (in a rectangular mode for the "x" and "y" axes) showing the relative repellency of VIOLIFF TM geraniol coeur, PAMPLEFLEUR ® and ORANGE FLOWER ETHER as well as the attractiveness of air. The graphs are based on experiments run for a total of one hour with six intervals of ten minutes each. The results are tabulated in Table IX, infra. This series of graphs is for the attractiveness or repellency as against mosquitoes (*Aedes aegypti*).

FIG. 5C is a series of graphs depicted in three dimensions (in a rectangular mode for the "x" and "y" axes) showing the relative repellency of VIOLIFF TM, geraniol coeur, PAMPLEFLEUR ® and ORANGE FLOWER ETHER as well as the attractiveness of air. The graphs are based on experiments run for a total of six hours with six intervals of one hour each. The results are tabulated in Table X, infra. This series of graphs is for the attractiveness or repellency as against mosquitoes (*Aedes aegypti*).

FIG. 5D is a series of graphs depicted in three dimensions (in a rectangular mode for the "x" and "y" axes) showing the relative repellency of ORANGE FLOWER ETHER, PAMPLEFLEUR ®, geraniol coeur, and VIOLIFF ™ as well as the attractiveness of air. The graphs are based on experiments run for a total of one hour with six intervals of ten minutes each. The results are tabulated in Table XI, infra. This series of graphs is for the attractiveness or repellency as against mosquitoes (*Aedes aegypti*).

FIG. 5E is a series of graphs depicted in three dimensions (in a rectangular mode for the "x" and "y" axes) showing the relative repellency of ORANGE FLOWER ETHER, PAMPLEFLEUR ®, geraniol coeur, and VIOLIFF ™ as well as the attractiveness of air. The graphs are based on experiments run for a total of six hours with six intervals of one hour each. The results are tabulated in Table XII, infra. This series of graphs is for the attractiveness or repellency as against mosquitoes (*Aedes aegypti*).

Figure 6:
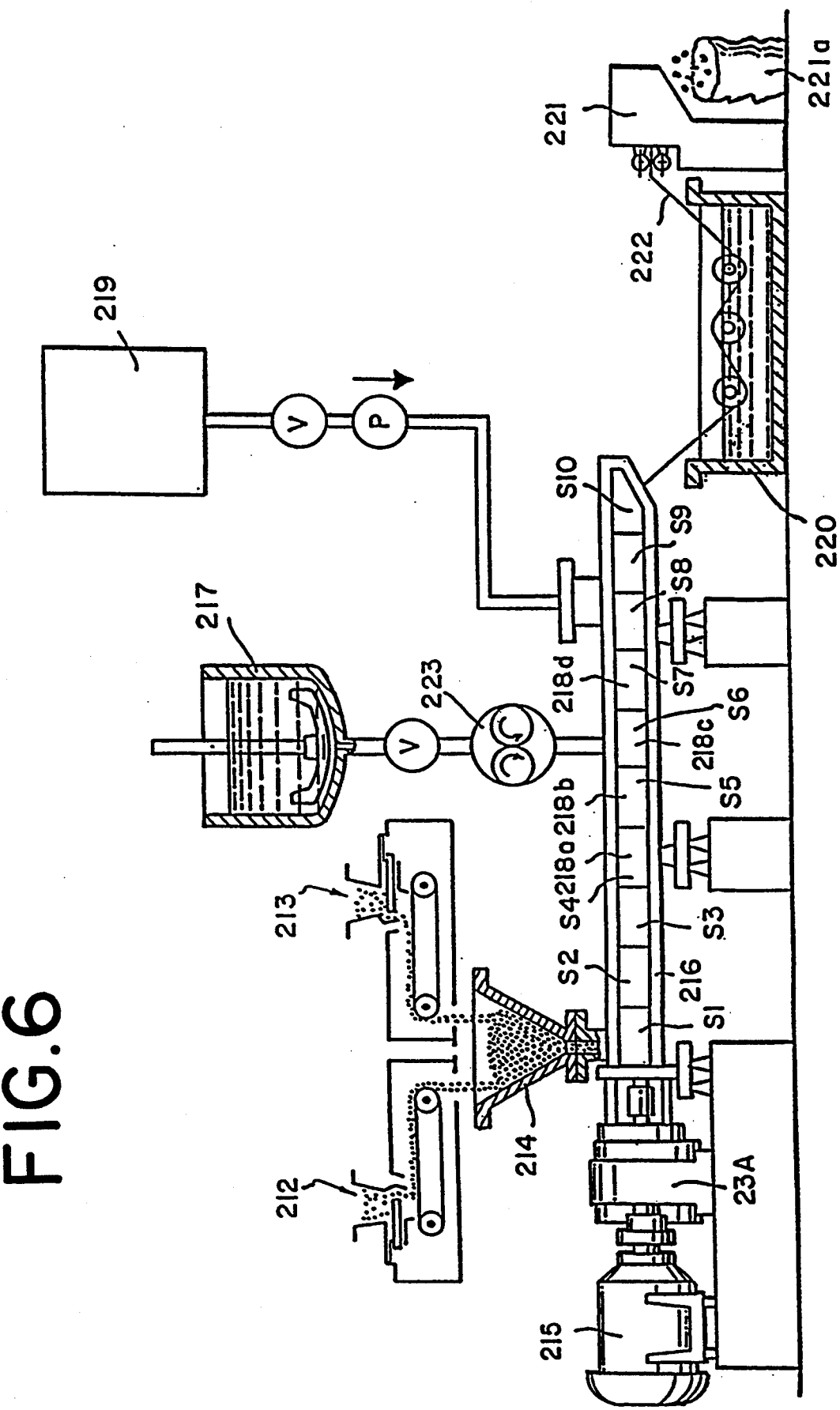

FIG. 6 is a cut-away side elevation schematic diagram of a screw extruder during the compounding of a resin with insect repellents, including one or more of the esters, alcohols or ether useful in our invention while simultaneously adding foaming agent into the hollow portion of the barrel of the extruder and incorporates the pelletizing apparatus used in the pelletizing of the extruded foamed tow product produced as a result of the extrusion operation.

Figure 7:
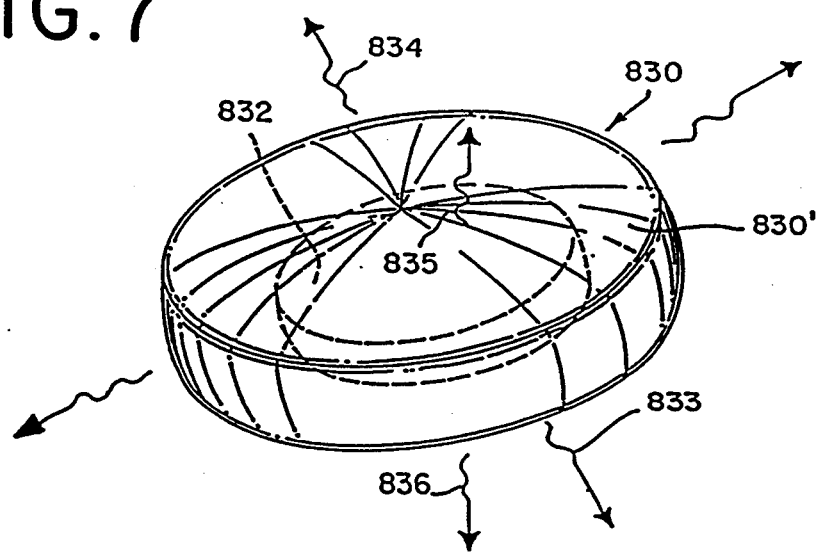

FIG. 7 is a perspective view of an ellipsodially-shaped detergent tablet containing a solid core which includes fused foamed polymeric particles which contain insect repellents which can be one or more of the esters, alcohols or ether our invention and, if desired, also containing an additional polymer, e.g., polyethylene. The polymer particles may, if desired, also contain additional aromatizing agents.

Figure 8:
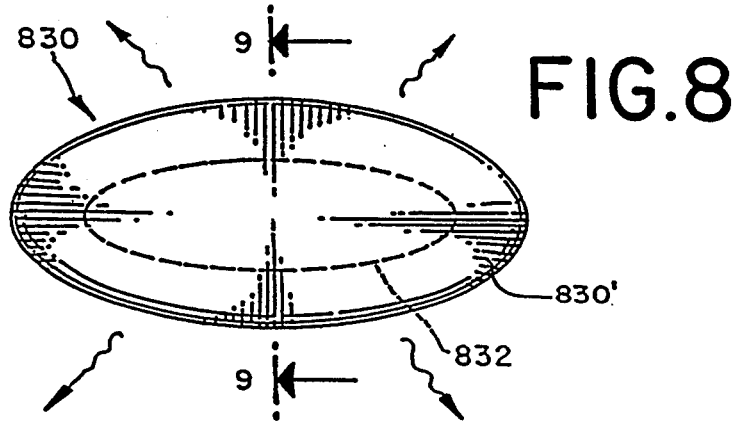

FIG. 8 is the top view of the ellipsodially-shaped detergent tablet of FIG. 7.

Figure 9:
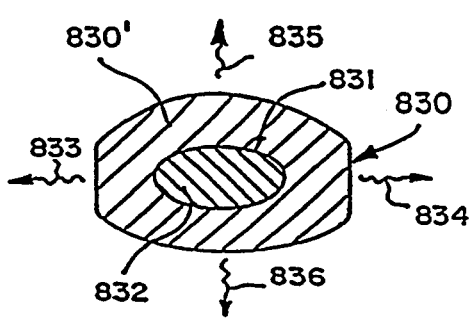

FIG. 9 is a cut-away front view of the ellipsodially-shaped detergent tablet of FIG. 7 in the direction of the arrows in FIG. 8.

Figure 10:
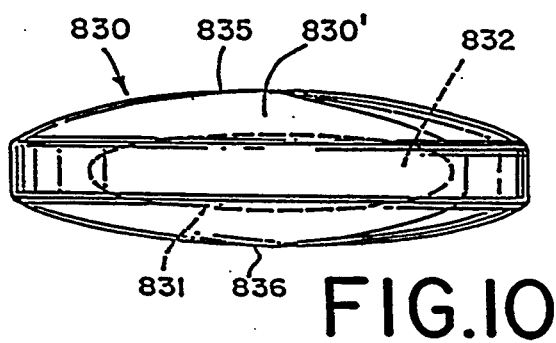

FIG. 10 is a side view of the ellipsodially-shaped detergent tablet of FIG. 8.

FIG. 11 is a perspective view of a rectangular parallelpiped-shaped detergent tablet containing a rectangular parallelpiped-shaped core comprising a major proportion of fused foamed polymeric particles which contain insect repellent, (e.g., one or more of the esters, alcohols or ether useful in our invention), e.g., the compound having the structure:

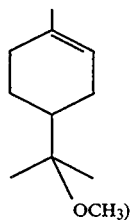

and may or may not be aromatized and, if desired, an additional polymer which may or may not contain insect repellent compositions and which may or may not be aromatized.

FIG. 12 is the top view of the rectangular parallelpiped-shaped detergent tablet of FIG. 11.

FIG. 13 is a cut-away front view of the rectangular parallelpiped-shaped detergent tablet of FIG. 11 looking in the direction of the arrows in FIG. 12.

FIG. 14 is a perspective view of an ellipsodially-shaped detergent tablet containing a hollow insect repellent agent (and, if desired, an aromatizing agent)-containing core which includes fused foamed polymeric particles. The insect repellent and, if desired, the aroma imparting agent is in the solid polymer and not in the void of the plastic core.

FIG. 15 is a top view of the ellipsodially-shaped detergent tablet of FIG. 14.

FIG. 16 is a front cut-away view of the ellipsodially-shaped detergent tablet of FIG. 14 looking in the direction of the arrows in FIG. 15, the core thereof being hollow and either containing an insect repellent material (and, if desired, an aroma imparting liquid) or, in the alternative, being a hollow core wherein the insect repellent material (and, if desired, the aroma imparting material) is in the solid fused foamed polymric particles which make up the core and wherein the void does not contain anything.

Figure 17:
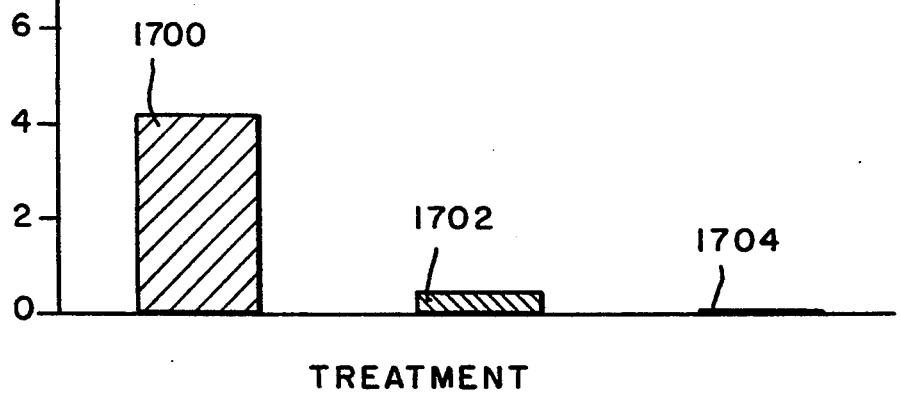

FIG. 17 is a bar graph showing a comparison of the field trial tests of repellents for mosquitoes, to wit:

(a') *Aedes aegypti;*
(b') *Aedes albopictus;*
(c') Anopheles spp.;
(d') Culex spp.;
(e') Aedes spp.;
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian;* comparing the use of VIOLIFF ™ and PAMPLEFLEUR ® as a repellent against a 50:50 mixture of air and CO$_2$. The "x" axis sets forth the mean number of mosquitoes trapped and the "y" axis sets forth the particular composition used in the treatment. The data was obtained using the apparatus of FIG. 1 described briefly, supra, and described in detail, infra.

Figure 18:
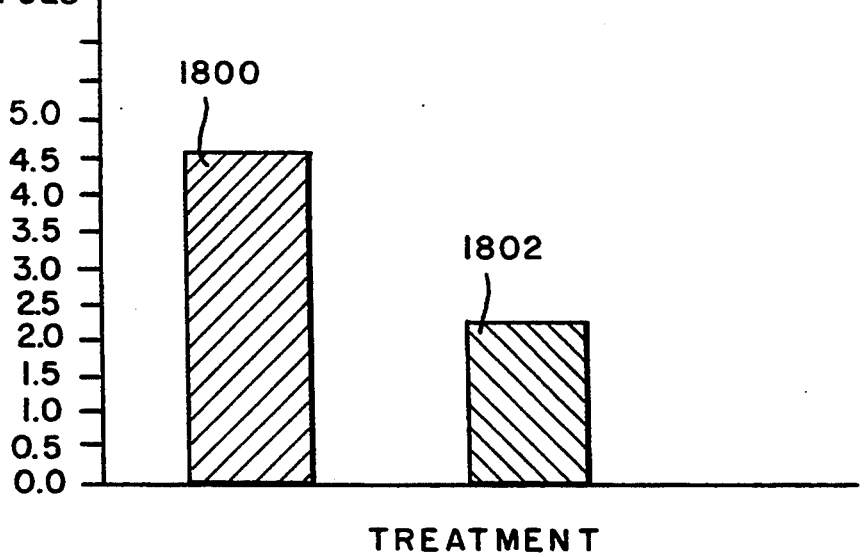

FIG. 18 is a bar garph showing a comparison of the field trial tests of air versus INDISAN ™ for mosquitoes, to wit:

(a') *Aedes aegypti;*
(b') *Aedes albopictus;*
(c') Anopheles spp.;
(d') Culex spp.;
(e') Aedes spp.;
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian.*

The mean number of mosquitoes is set forth on the "y" axis and the composition used in the treatment is set forth on the "x" axis. The data was obtained using the apparatus of FIG. 1. FIG. 19 is a bar graph showing a comparison of the field trial tests using the apparatus of FIG. 1 of the repellent, VIOLIFF ™ versus the attractant, air. The mean number of mosquitoes, to wit:

(a') *Aedes aegypti;*

(b') *Aedes albopictus;*
(c') *Anopheles spp.;*
(d') *Culex spp.;*
(e') *Aedes spp.;*
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian;*
is set forth on the "y" axis and the composition used in the treatment, e.g., air or VIOLIFF ™ is set forth on the "x" axis.

FIG. 20 is a bar graph showing a comparison of the field trial tests using the apparatus of FIG. 1 of the repellents geraniol coeur and PAMPLEFLEUR® having the structure:

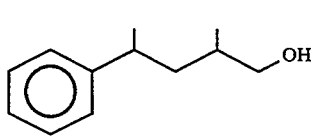

versus the attractant, a 50:50 mixture of air and $CO_2$. The mean number of the mosquitoes, to wit:
(a') *Aedes aegypti;*
(b') *Aedes albopictus;*
(c') *Anopheles spp.;*
(d') *Culex spp.;*
(e') *Aedes spp.;*
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian;*
is set forth on the "y" axis and the treatment composition, e.g., the 50:50 mixture of air and $CO_2$, is set forth on the "x" axis.

Figure 21:
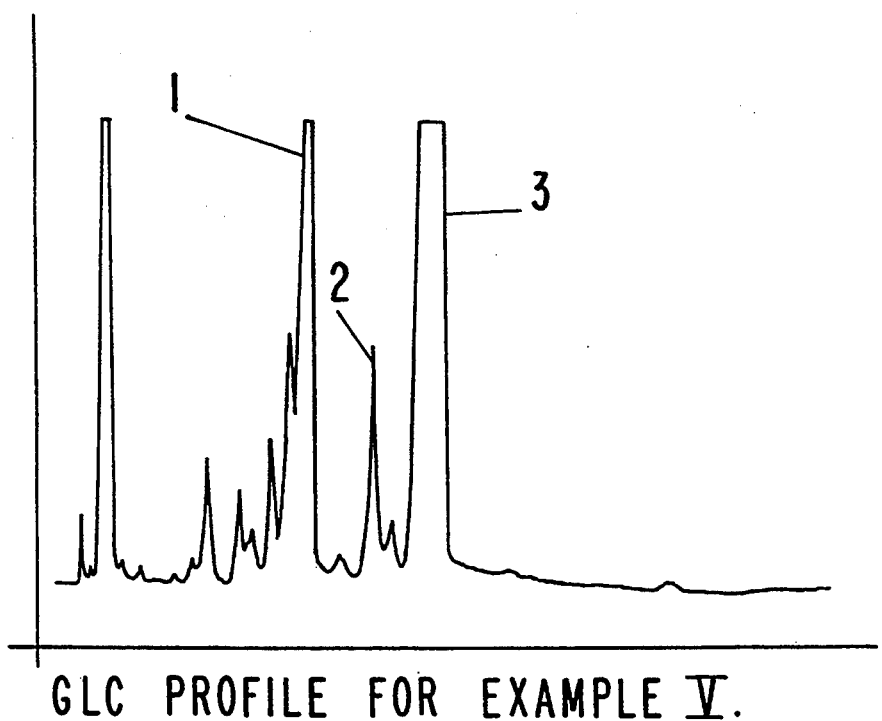

FIG. 21 is the GLC profile for the reaction product of Example V containing the compounds having the structures:

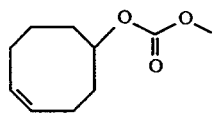

and

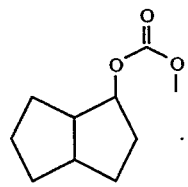

Figure 22:
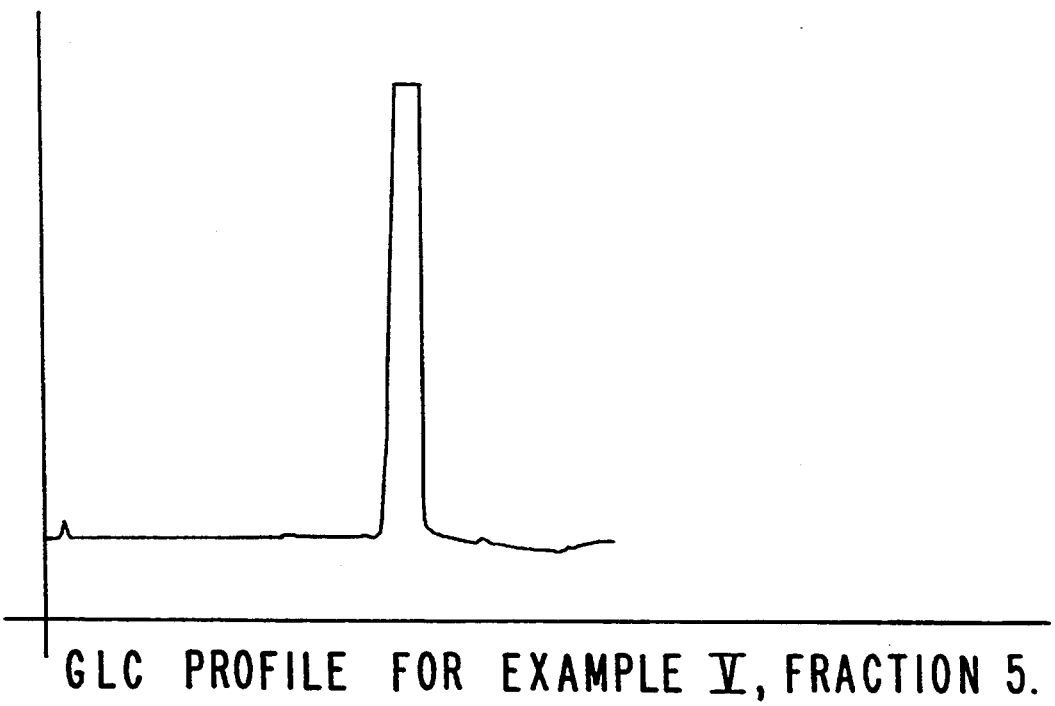

FIG. 22 is the GLC profile for Fraction 13 of the distillation product of the reaction product of Example V containing the compounds having the structures:

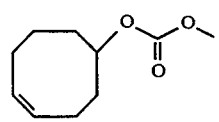

and

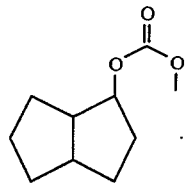

Figure 23:
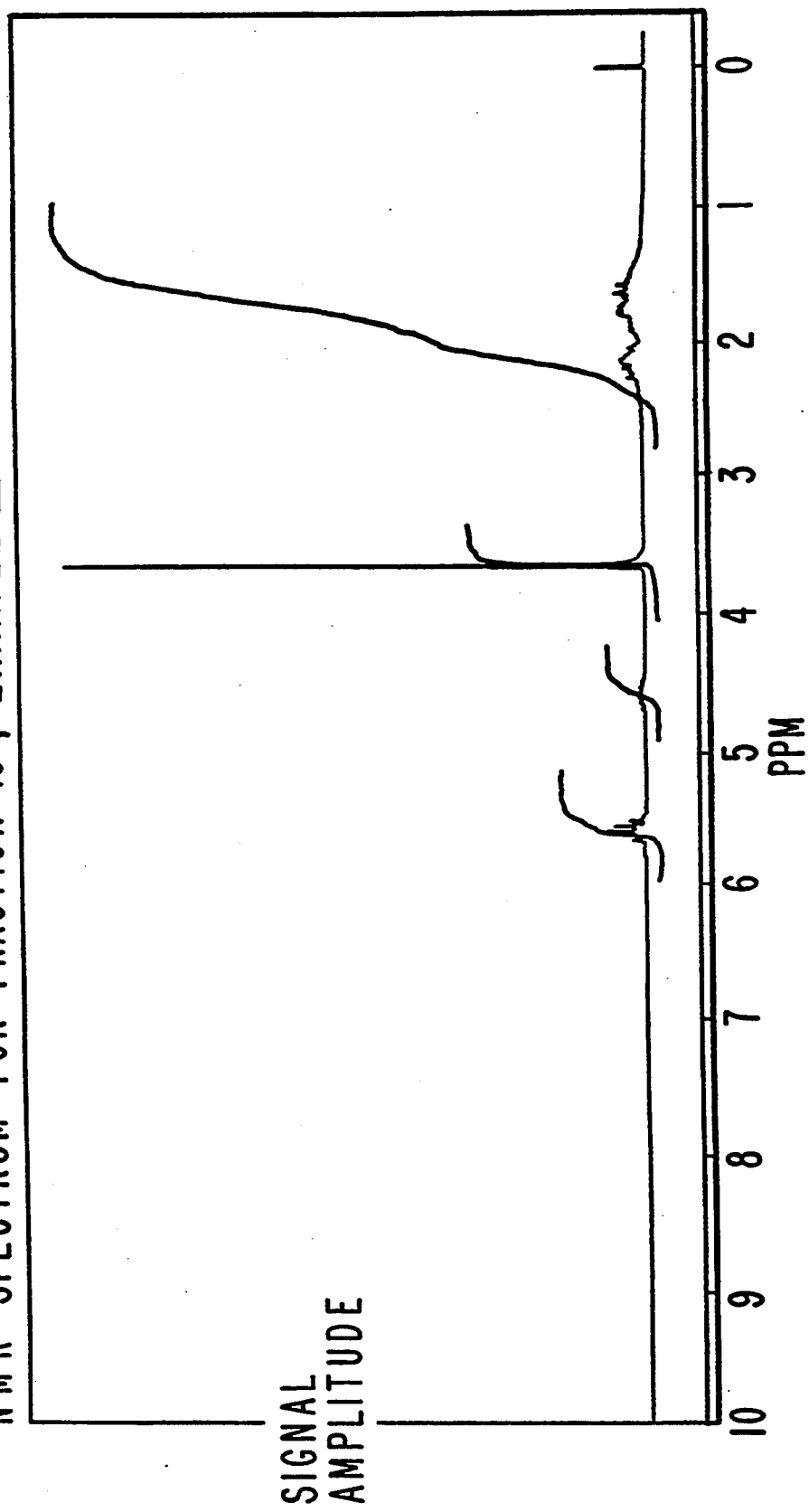

FIG. 23 is the NMR spectrum for Fraction 13 of the distillation product of the reaction product of Example V containing the compounds having the structures:

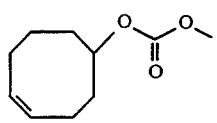

and

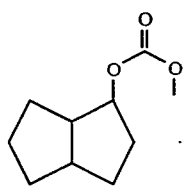

Figure 24:
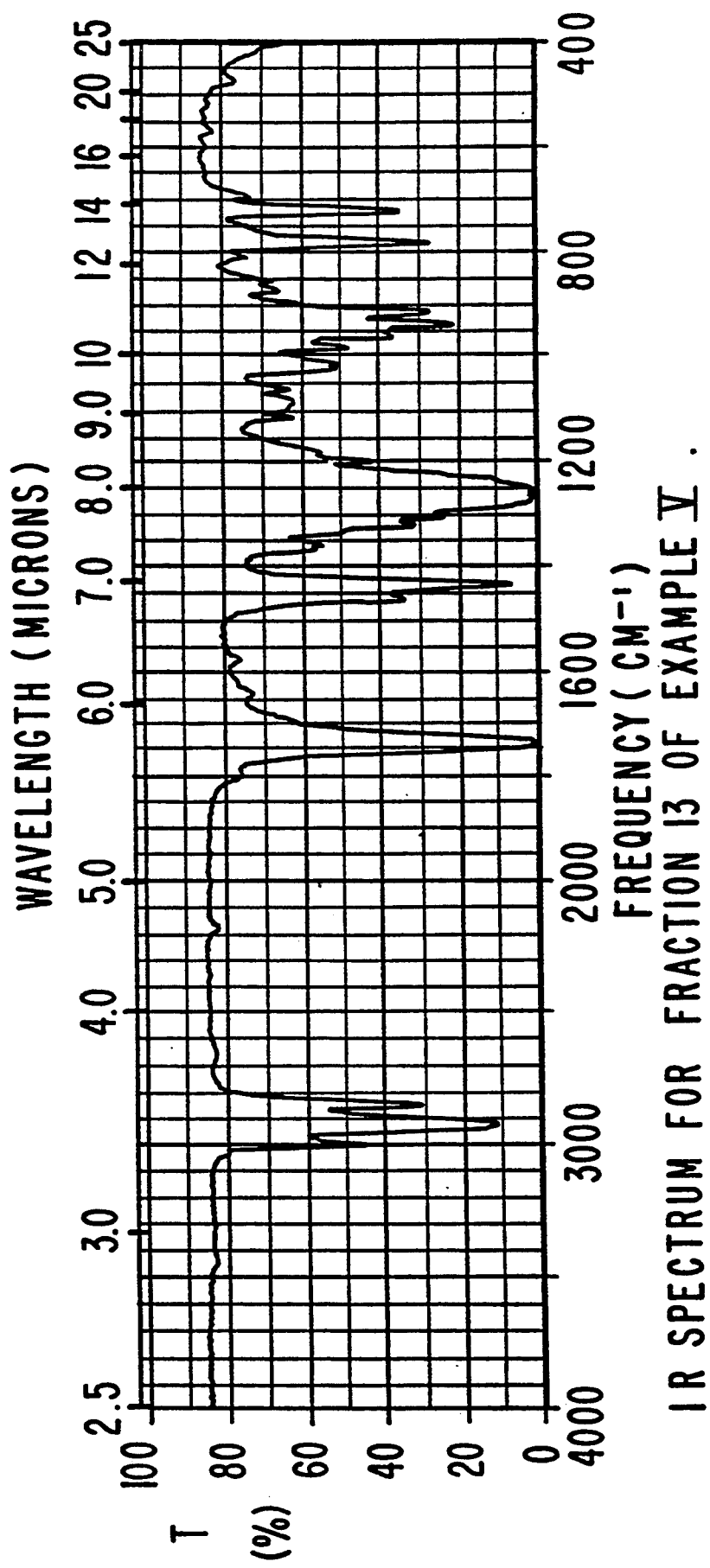

FIG. 24 is the infrared spectrum for Fraction 13 of the distillation product of the reaction product of Example V containing the compounds having the structures:

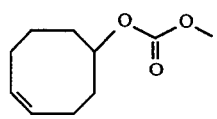

and

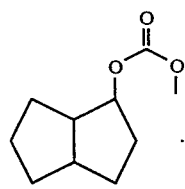

Figure 25:
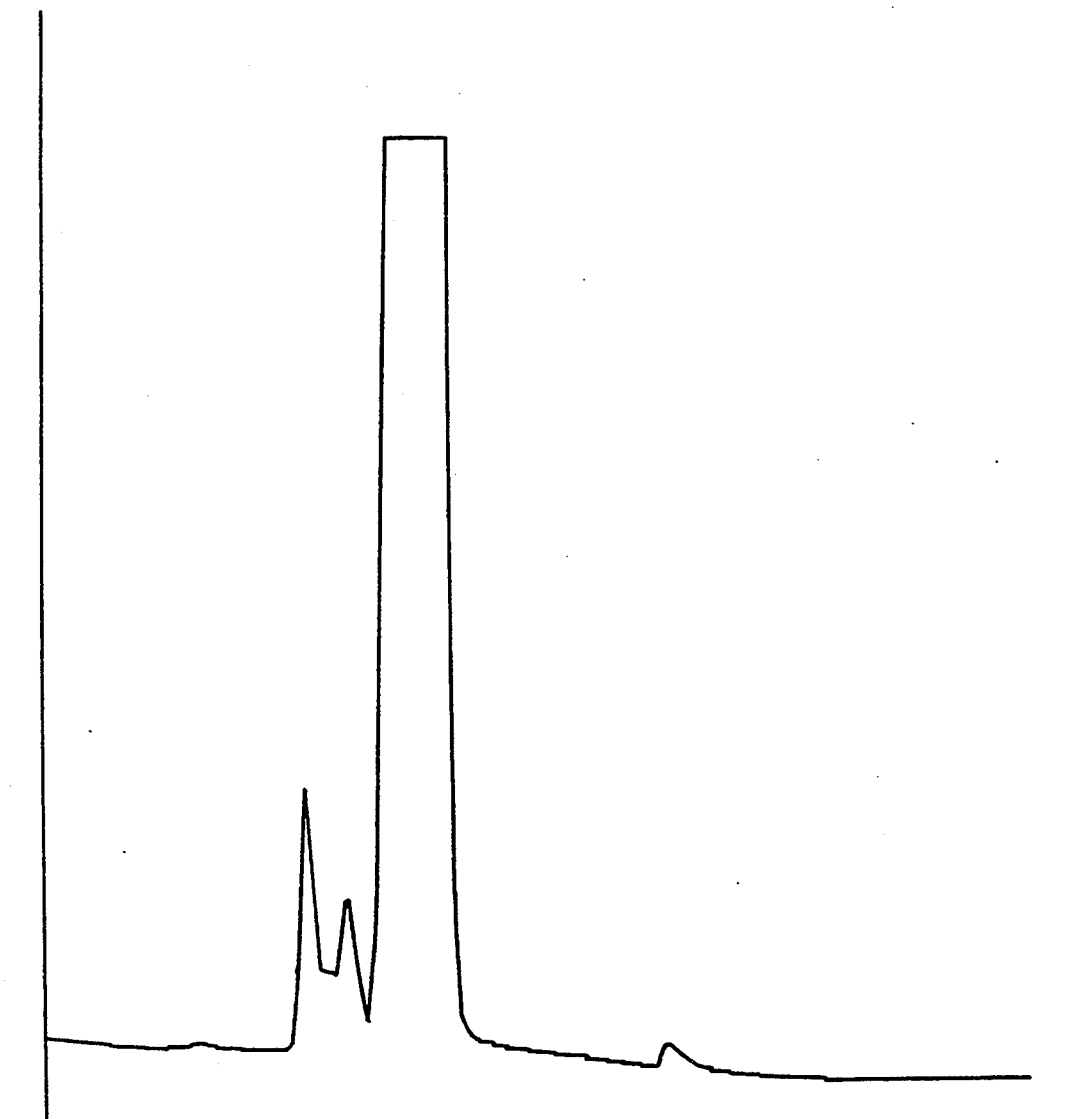

FIG. 25 is the GLC profile for Fraction 7 of the distillation product of the reaction product of Example V containing the compound having the structure:

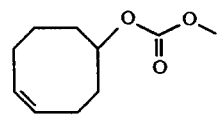

in major proportion and the compound having the structure:

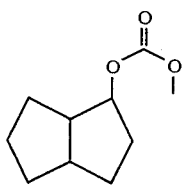

in minor proportion.

Figure 26:
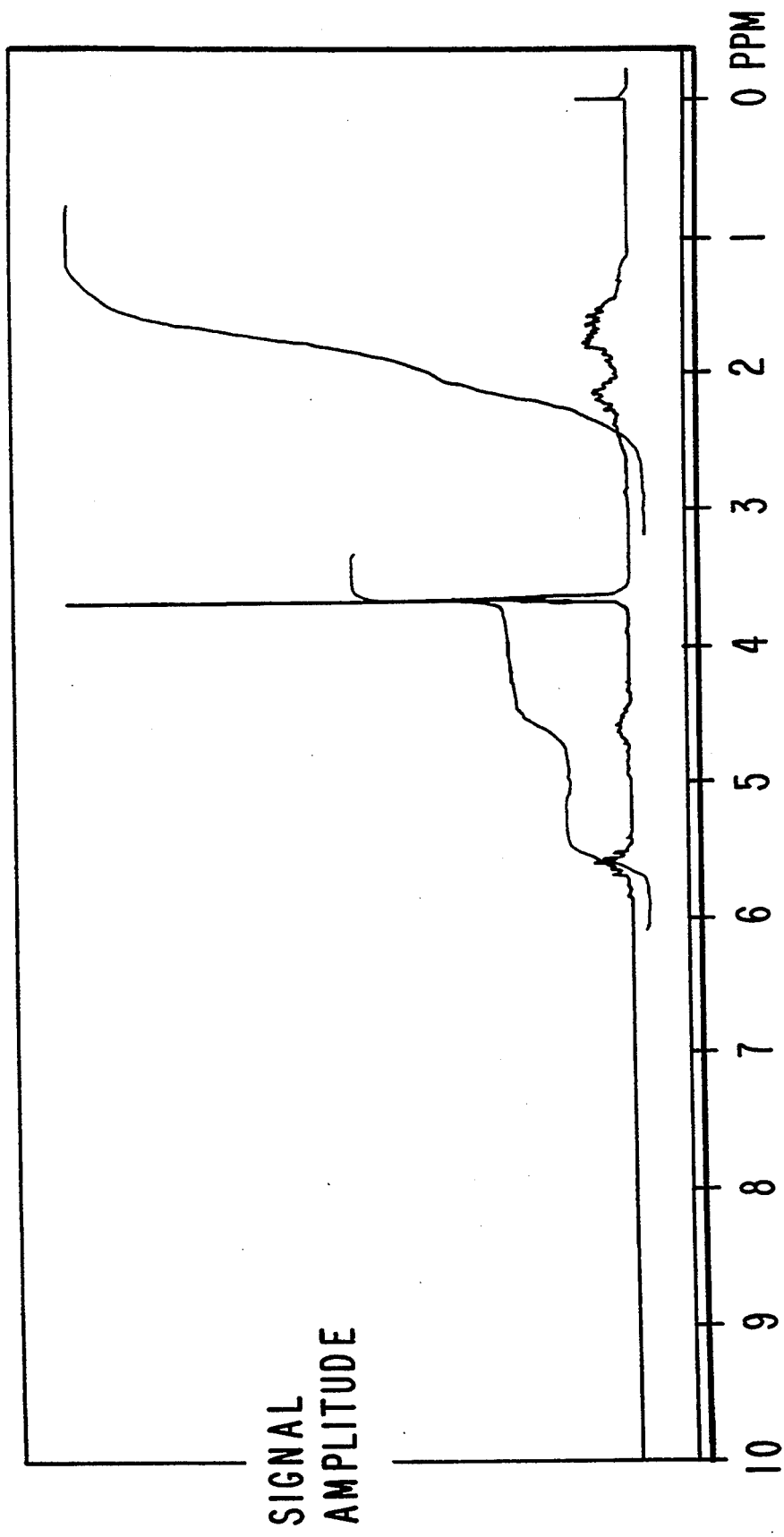

FIG. 26 is the NMR spectrum for Fraction 7 of the distillation product of the reaction product of Example V containing the compound having the structure:

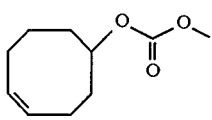

in major proportion and the compound having the structure:

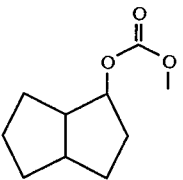

in minor proportion (Solvent: CFCl₃; field strength: 100 MHz).

Figure 27:
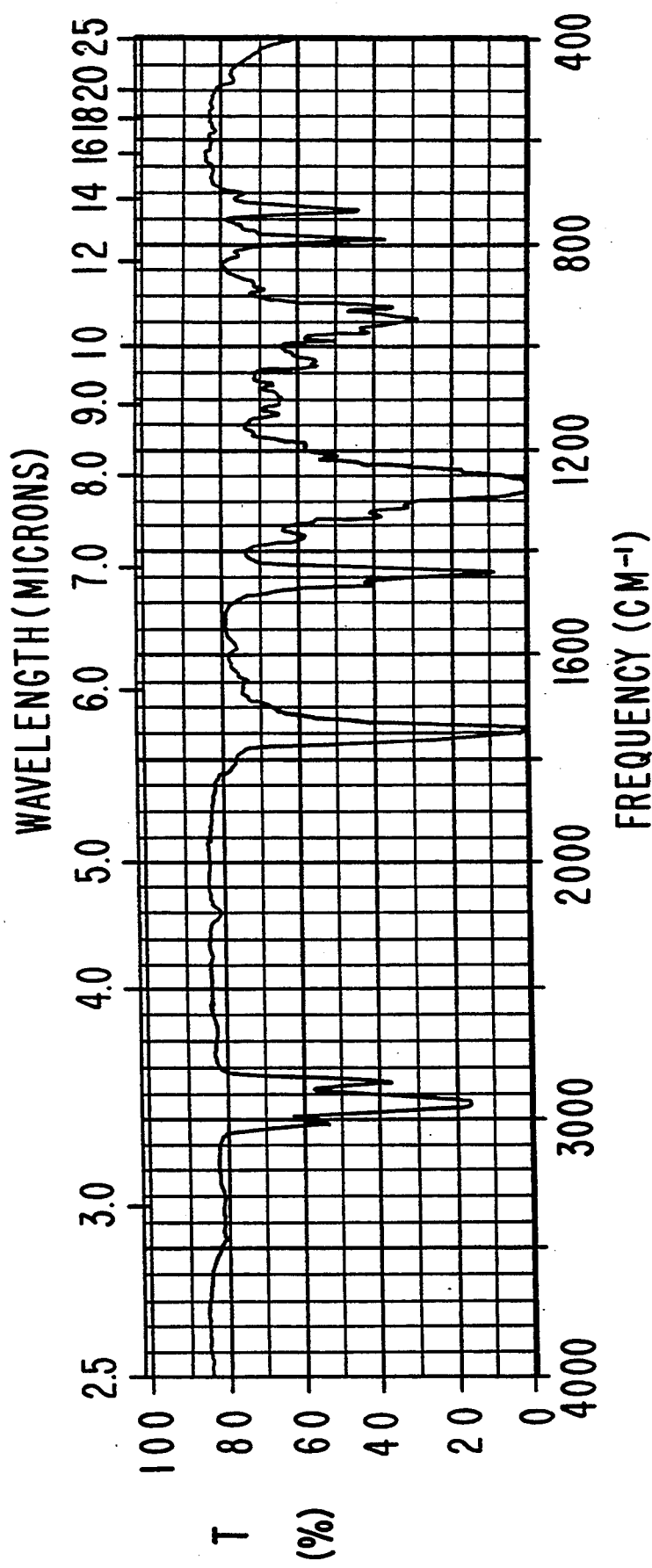

FIG. 27 is the infrared spectrum for Fraction 7 of the distillation product of the reaction product of Example V containing the compound having the structure:

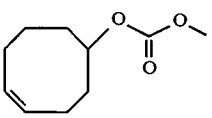

in major proportion and the compound having the structure:

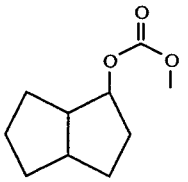

in minor proportion (ratio of compound having the structure:

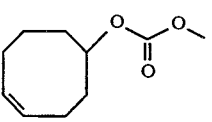

to compound having the structure:

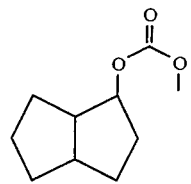

being 77:19).

Figure 28:
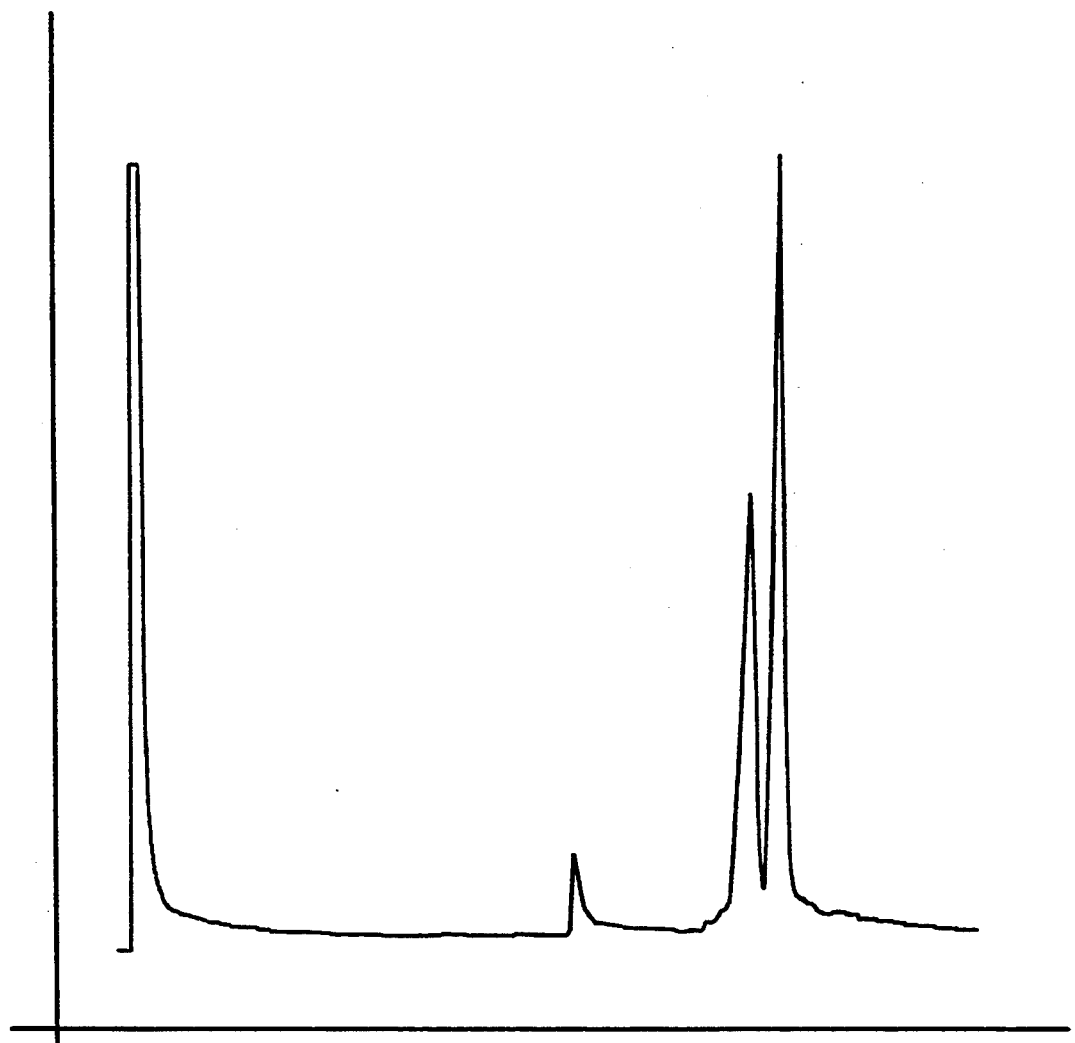

FIG. 28 is the GLC profile for INDISAN ™ containing a major proportion of the compound having the structure:

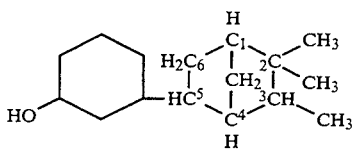

prepared by the steps of:
(i) reacting guiacol with camphene in the presence of a Friedel-Crafts catalyst to form an alkylation product;
(ii) treating the alkylation product with hydrogen to form a dioxy intermediate; and
(iii) treating the dioxy intermediate with hydrogen to form a meta-(isocamphyl-5)cyclohexanol-containing mixture.

Figure 29:
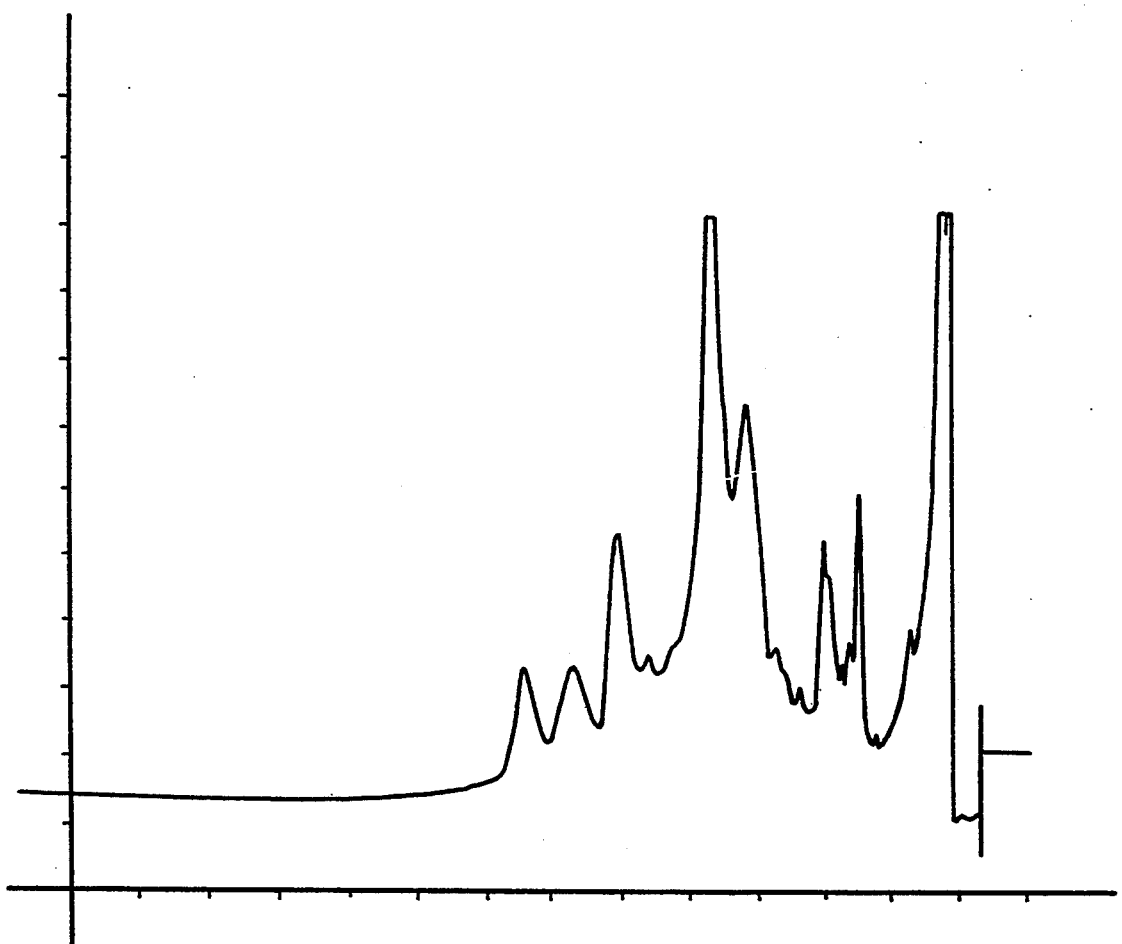

FIG. 29 is the GLC profile of the reaction product of the second stage of the hydrogenation of Example VI containing a major proportion of the compound having the structure:

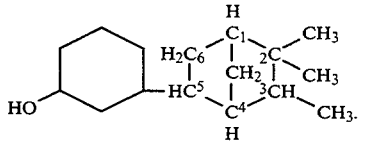

Example VI corresponds to Example XIII of U.S. Pat. No. 4,014,944 issued on Mar. 29, 1977, the specification for which is incorporated hereby by reference herein.

DETAILED DESCRIPTION OF THE DRAWINGS

Referring to FIG. 1, a semiochemical field trap 100 for blood feeding arthropods 29 comprises:

(1) An upright vertically-disposed first hollow outer housing 28 having substantially rigid arthropod-impermeable first side walls 28b, an upper arthropod-horizontal surface 28a substantially entirely contiguous with said first side walls 28b and a substantially entirely open bottom 28d having a substantially horizontal plane substantially perpendicular to the vertical axis 28c of said first hollow outer housing 28;

(2) Located along an axis 28c substantially perpendicular to the horizontal plane 28d of said substantially entirely open bottom of said first outer housing 28, substantially parallel to the vertical axis 28c of said first hollow housing 28, and within said first hollow housing 28, a second inner hollow housing 37, having a hollow interior, opposite open upper first and lower second ends, vertically-disposed rigid, arthropod-impenetrable side walls 37a, and a longitudinal dimension extending between the two ends, said upper first end being at a substantial distance below said upper substantially horizontal surace 28a of said first outer housing 28;

(3) Extending outwardly from said substantially vertically disposed side walls 37a of said second inner hollow housing 37 to the side walls 28b of the first hollow outer housing 28, at an angle of from about −5° C. up to about −40° C., measured downwardly from the substantially horizontal plane 28 of the open bottom of said first hollow outer housing 28, substantially rigid rib components 27, which enabled the fixed positioning of said inner hollow housing 37 with respect to the positioning of and within said outer hollow housing 28;

(4) Completely encompassingly traversing in a substantially tight fitting manner the area between (i) the first side walls 28b of said first outer hollow housing 28, and (ii) the second side walls 38a of said second inner hollow housing 37 along the directional vectors of said rib components 27 and in a curvilinear plane below and substantially contiguous to said rib components 27, a continuous substantially macroporous mesh substance 24, having such a mesh size as to be impenetrable by arthropods 29 sought to be entrapped, but pervious to gas and liquid and, in addition, radiation transmittable, and capable of supporting a matrix article, as indicated by reference numerals 26, 26a and 26b containing substainably releasable semiochemical;

(5) At least one semiochemical-containing matrix 26, 26a, and 26b comprising a porous containment agent containing in the interstices thereof at least one semiochemical sustainably releasable therefrom, located on the upper surface of said macroporous mesh substance, 24;

(6) A sustainably vertically disposed drive shaft 43 supported for rotary motion about its axis 28c, extending from below and into the hollow interior of said inner hollow housing 37 along the side longitudinal dimension thereof;

(7) Motor means 35 connected to a first lower end of said drive shaft 43 for rotating said drive shaft 43 about its axis 28c;

(8) Air flow creation means 36 attached to the second upper end of said drive shaft 43, being of such a design whereby the rotation of said drive shaft 43 directly causes the rotation of said air flow creation means 36 and induces the flow of air 34 from beneath said second inner hollow housing upwardly into the 3-space 52, 54 within said first hollow outer housing 28 between the outer side wall of the second inner hollow housing 37 and the inner side-wall 28b of said first outer hollow housing 28;

(9) Radiation emission means 20 for emission of radiation 20r of a specific wave length or of a range of wave lengths outwardly from the apparatus 100 located in the vicinity of the lower portion of said second inner hollow housing 37, below the location of said 27;

(10) Radiation pulsing means 4201 connected via connections 4250 to said radiation means 20 causing said radiation 20r to have a frequency minicking insect wing beat and/or insect visual sensing frequencies;

(11) At least one power supply means 14, 16 associated with with said trap 100 energizing said radiation means 20, said radiation pulsing means 4201 and said motor means 35 on engagement of the power supply 14, 16 with said motor means 35, said radiation pulsing means 4201 and said radiation emission means 20 whereby arthropods 29b in the vicinity of said trap 100 are attracted by said pulsed radiation 20r to a location so close to said trap 100 that in the event that an attracting chemical in said matrix 26, 26a, 26b detected by said arthropods 29b, said arthropods will enter the air stream 34 created by said air flow creation means 36 (or 50:50 volume:volume air:CO$_2$ flow creation means 36), and be carried through location 41 into the 3-space 52, 54 within said first hollow outer housing 28 between the outer side wall 37a of said inner hollow housing 37 and the inner side wall 28b of said first outer hollow housing 28.

Referring to the carbon dioxide flow, dry ice particles 69 or "chunks" is placed into zipper-locked bag 64 with zip-lock 67. The bag is connected to tube 62, and tube 62 is mounted at mount 66 beneath cylinder 37 and the cylinder 12 which holds the power supply means 14, 16, and motor means 35 together with radiation pulsing means 4201. The zip-locked bag 64 is contained in insulated container 68. As soon as the switch 18 is turned on in order to engage power supply means 14, 16 with motor means 35 and radiation pulsing means 4201, a pinch clamp is removed from tube 62 enabling carbon dioxide to flow through tube 62 into the 3-space surrounding propeller 36 at location 41. The carbon dioxide alone acts as an attractant for the species of insects:

(a) *Musca domestica* L.(Diptera:Muscidae);
(b) *Aedes aegypti;*
(c) *Aedes albopictus;*
(d) Anopheles spp.;
(e) *Coquillettidia perturbans;*
(f) Culiseta Spp.;
(g) Culex spp.;
(h) Psorophora spp.;
(i) Culicoides spp.; and/or
(j) Lutzomyia spp.;
(k) Aedes spp.;
(l) *Culex nigripalpus;*
(m) *Aedes atlanticus;*
(n) *Culex salinarius;*
(o) *Aedes vexans;*
(p) Simuliidae spp.;
(q) *Psorohora ferox;*
(r) *Aedes infirmatus;*
(s) *Drosophila melanogaster;*
(t) Coccinellidae;
(u) *Anopheles crucian;*
(v) *Psorophora columbiae;* and
(w) *Haemotobia irritans* (L.)

If desired, the trap 100 may also or in the alternative to being placed in the ground through stake 42, be suspended from suspension 30 held by clips 32.

Figure 2:
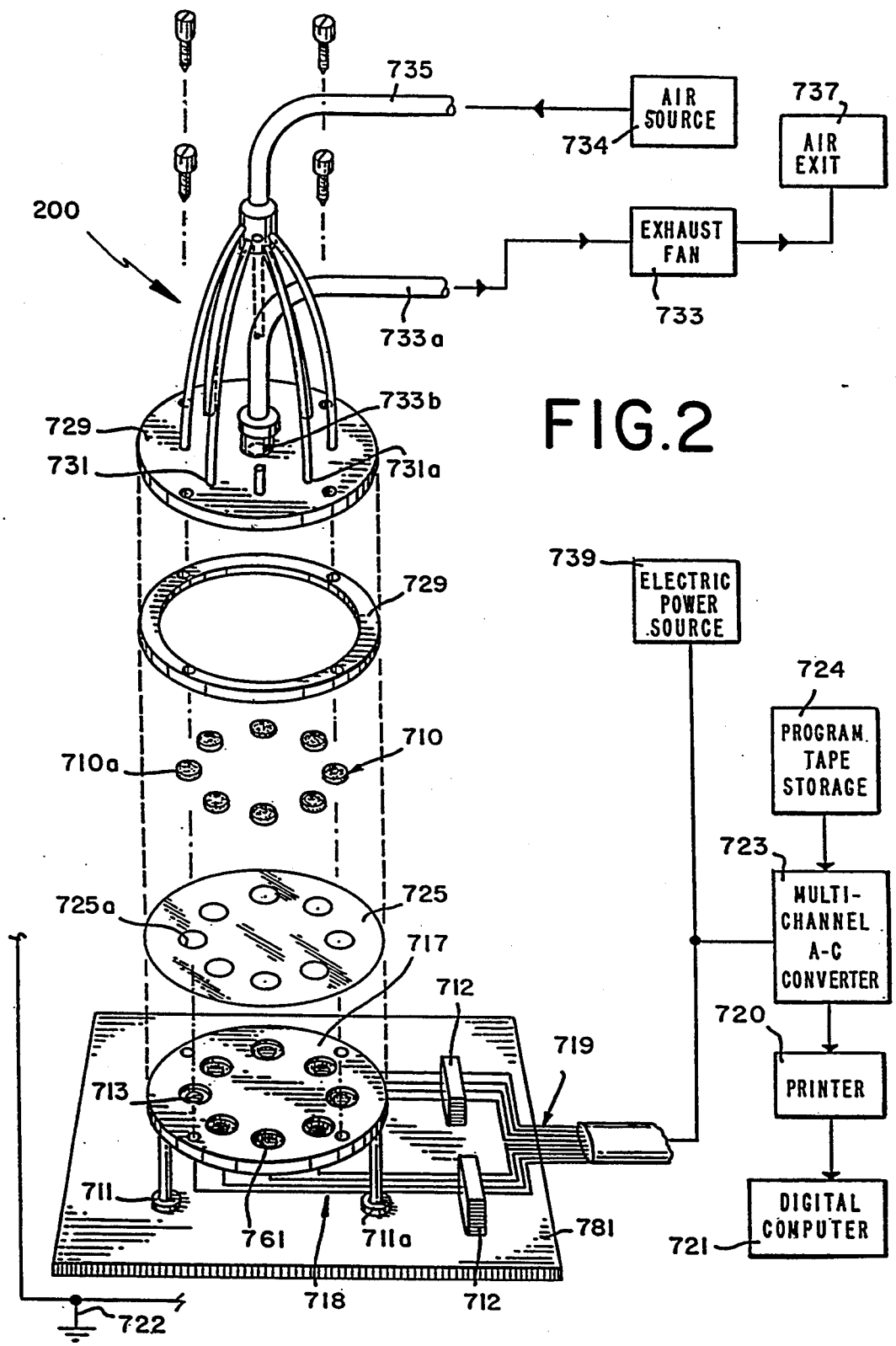

The olfactometer illustrated in FIG. 2 and the olfactometer section illustrated in FIG. 2A are described in U.S. Pat. No. 4,748,860 issued on Jun. 7, 1988 the specification for which is incorporated herein by reference.

In FIG. 2, air source 734 feeds air through line 735 through air distributors 736, 736a, et seq. onto base plate 717, containing insect landing sites 710, 710a, et seq. The base plate 717 is separated from the spacer plate 729 for the air lines 736, 736a, et seq. whereby the air lines 736, 736a, et seq. are held in place at positions 731 and 731a. Air exits through line 733a using exhaust fan 733. The olfactometer is assisted with computer apparatus shown in schematic form and block flow diagram form using reference numerals 720, 721, 723, 724 and 739. Dampers 711a, 711b, et seq. hold base plate 717 in place horizontally. When an insect lands on sensor landing site 710, 710a et seq. the landing is recorded electrically through a sensor shown in magnified form in FIG. 14A. The sensor landing site includes a transducer 713 and causes an electrical impulse to proceed through wire 718 and then through wire 719 to a multi-channel A-D converter 723 (using electric power source 739) which is associated with program tape storage 724, printer 720 and digital computer which is associated with modem and main frame 721. Reference numeral 722 shows a "Faraday" cage completing the olfactometer circuit. The electical impulse thus effects a recording of data as set forth in FIGS. 3A, 3B and 4A.

FIG. 2A is a detailed section showing one specific landing site 710a of FIG. 2 on which the insect lands if attracted by one of the ester, alcohol and/or ether (e.g., the compound having the structure:

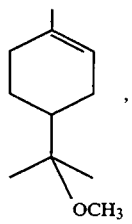

-containing compositions of our invention taken alone or in admixture or does not land if repelled by, for example, one or more of the ester, alcohol and/or ether compositions of our invention taken alone or in admixture. At other landing sites nothing is located (and these are the "control" landing sites). At other sites a second repellent can be located, or an attractant can be located. The olfactometer includes a base 781 on which the damper 711a, 711b, et seq. are located namely base 781. Base plate 717 is preferably covered with a film such as SARAN WRAP® 725 so that any insects that are attracted to the landing sites are not distracted to any other areas on base plate 717.

FIG. 3A and 3B are bar graphs of number of feeding contacts by mosquitoes (Aedes aegypti) on the "y" axis versus treatment composition (on the "x" axis) using the apparatus of FIG. 2. FIG. 3A sets forth mosquito contacts for a mean one hour feeding period. FIG. 3B sets forth the mosquito contact for a mean 2-6 hour contact period. The bar indicated by reference numerals 301a and 301b are for clean air. The bars indicated by reference numerals 302a and 302b are for diethyl phthalate.

FIGS. 4A, 4B, 4C, 4D, 4E, 4F and 4G show repellency against house flies (Musca domestica L.(Diptera:-Muscidae)) for FIG. 4A; horn flies (Haemotobia irritans (L.) for FIG. 4B; and mosquitoes (Aedes aegypti) for FIGS. 4C, 4D, 4E, 4F and 4G of INDISAN TM (the graphs indicated by reference numerals 404a, 404b, 404c, 404d, 404e, 404f and 404g. The graphs indicated by reference numerals 402a, 402b, 402c, 402d, 402e, 402f and 402g show the attractiveness of air itself. The graphs are series of graphs depicting in three dimensions (in a rectangular mode for the "x" and "y" axis) the repellency of INDISAN TM and the attractancy of air per se.

The graph of FIG. 4A shows repellency against house flies (Musca domestica L.(Diptera:Muscidae)). The data supporting the graph of FIG. 4A is set forth in Table I as follows:

TABLE I

| Composition Tested | Reference Numeral For Graph | Insects Per Interval (10 Minute Intervals Totalling One Hour) | | | | | |
|---|---|---|---|---|---|---|---|
| *MUSCA DOMESTICA L.* (DIPTERA:MUSCIDAE) | | | | | | | |
| INDISAN TM | 404A | 0 | 1 | 0 | 0 | 1 | 0 | 2 |
| Air | 402A | 0 | 0 | 466 | 376 | 288 | 206 | 173 |

The data supporting the graph of FIG. 4B for horn flies (*Haemotobia irritans* (L.)) is set forth in Table II as follows:

TABLE II

| Composition Tested | Reference Numeral For Graph | Insects Per Interval (10 Minute Intervals Totalling One Hour) | | | | | |
|---|---|---|---|---|---|---|---|
| (*HAEMOTOBIA IRRITANS (L.)*) | | | | | | | |
| INDISAN TM | 404B | 0 | 42 | 7 | 9 | 4 | 2 | 11 |
| Air | 402B | 0 | 126 | 145 | 334 | 270 | 356 | 525 |

FIG. 4C shows experiments run for a period of one hour with six intervals of ten minutes each. The data supporting the graph of FIG. 4C are set forth in Table III as follows:

TABLE III

| Composition Tested | Reference Numeral For Graph | Insects Per Interval (10 Minute Intervals Totalling One Hour) | | | | | |
|---|---|---|---|---|---|---|---|
| (*AEDES AEGYPTI*) | | | | | | | |
| INDISAN TM | 404C | 0 | 9 | 12 | 15 | 11 | 9 | 2 |
| Air | 402C | 0 | 173 | 298 | 207 | 367 | 323 | 431 |

The data supporting the graph of FIG. 4D is set forth in Table IV, for mosquitoes. The graphs are based on experiments run for a period of twelve hour with six intervals of two hours each. The data supporting the graph of FIG. 4D is set forth in Table IV as follows:

TABLE IV

| Composition Tested | Reference Numeral For Graph | Insects Per Interval (Two Hour Intervals Totalling Twelve Hours) | | | | | |
|---|---|---|---|---|---|---|---|
| (*AEDES AEGYPTI*) | | | | | | | |
| INDISAN TM | 404D | 0 | 49 | 8 | 3 | 2 | 0 | 1 |
| Air | 402D | 0 | 82 | 95 | 82 | 12 | 99 | 5 |

FIG. 4E shows repellency against mosquitoes (*Aedes aegypti*) by INDISAN TM and attractiveness by air. The graphs are based on experiments run for a period of one hour with six intervals of ten minutes each. The data supporting the graph of FIG. 4E is set forth in Table V as follows:

TABLE V

| Composition Tested | Reference Numeral For Graph | Insects Per Interval (Ten Minute Intervals Totalling One Hour) | | | | | |
|---|---|---|---|---|---|---|---|
| (*AEDES AEGYPTI*) | | | | | | | |
| INDISAN TM | 404E | 0 | 5 | 3 | 0 | 0 | 0 | 6 |
| Air | 402E | 0 | 281 | 507 | 290 | 205 | 243 | 84 |

FIG. 4F shows repellency of (*Aedes aegypti*) mosquitoes by INDISAN TM and attractiveness by air. The graphs are based on experiments run for a period of one hour with six intervals of ten minutes each. The data supporting the graph of FIG. 4F is set forth in the following Table VI:

TABLE VI

(AEDES AEGYPTI)

| Composition Tested | Reference Numeral For Graph | Insects Per Interval (10 Minute Intervals Totalling One Hour) | | | | | | |
|---|---|---|---|---|---|---|---|---|
| INDI-SAN TM | 404F | 0 | 0 | 0 | 0 | 0 | 0 | 0 |
| Air | 402F | 0 | 480 | 441 | 531 | 531 | 387 | 488 |

FIG. 4G are graphs showing the repellency of (Aedes aegypti) by INDISAN TM and attractiveness by air. The graphs are based on experiments run for a period of twelve hours with six intervals of two hours each. The data supporting the graph of FIG. 4G is set forth in Table VII as follows:

TABLE VII

(AEDES AEGYPTI)

| Composition Tested | Reference Numeral For Graph | Insects Per Interval (10 Minute Intervals Totalling one Hour) | | | | | | |
|---|---|---|---|---|---|---|---|---|
| INDI-SAN TM | 404G | 0 | 1 | 0 | 0 | 0 | 0 | 0 |
| Air | 402G | 0 | 1616 | 1567 | 1466 | 1295 | 1211 | 502 |

FIGS. 5A, 5B, 5C, 5D and 5E show relative repellencies against mosquitoes (Aedes aegypti) ) of ORANGE FLOWER ETHER having the structure:

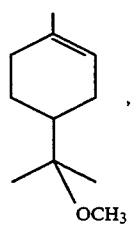

PAMPLEFLEUR ® having the structure:

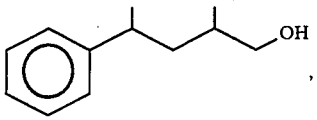

VIOLIFF TM having as its main constituent the compound having the structure:

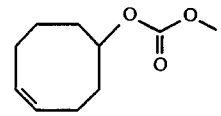

and in the case of FIG. 5B, 5C, 5D and 5E, geraniol coeur, as well as air per se. FIGS. 5A, 5B, 5C, 5D and 5E are series of graphs each depicting in three dimensions (in a rectangular mode for the "x" and "y" axes) the relative attractiveness or repellency of the ORANGE FLOWER ETHER, PAMPLEFLEUR ®, VIOLIFF TM and geraniol coeur.

The graphs for FIG. 5A are based on experiments run for a period of one hour with six intervals of ten minutes each. The data supporting the graph of FIG. 5A is set forth in Table VIII as follows:

TABLE VIII

(AEDES AEGYPTI)

| Composition Tested | Reference Numeral For Graph | Insects Per Interval (Two Hour Intervals Totalling Twelve Hours) | | | | | | |
|---|---|---|---|---|---|---|---|---|
| ORANGE FLOWER ETHER | 503A | 0 | 1 | 0 | 0 | 1 | 0 | 0 |
| PAMPLE-FLEUR TM | 504A | 0 | 0 | 0 | 0 | 0 | 0 | 0 |
| VIOLIFF TM | 505A | 0 | 6 | 3 | 0 | 0 | 0 | 0 |
| Air | 502A | 0 | 17 | 62 | 114 | 45 | 88 | 36 |

Referring to FIG. 5B, the graphs are based on experiments run for a period of one hour with six intervals of ten minutes each. The data supporting the graph of FIG. 5B is set forth in Table IX as follows:

TABLE IX

(AEDES AEGYPTI)

| Composition Tested | Reference Numeral For Graph | Insects Per Interval (Two Hour Intervals Totalling Twelve Hours) | | | | | | |
|---|---|---|---|---|---|---|---|---|
| ORANGE FLOWER ETHER | 503B | 0 | 5 | 0 | 2 | 6 | 5 | 11 |
| PAMPLE-FLEUR ® | 504B | 0 | 1 | 48 | 38 | 4 | 56 | 8 |
| VIOLIFF TM | 505B | 0 | 2 | 0 | 0 | 9 | 15 | 0 |
| geraniol coeur | 506B | 0 | 0 | 3 | 1 | 59 | 0 | 7 |
| Air | 502B | 0 | 10 | 65 | 121 | 491 | 267 | 248 |

Referring to FIG. 5C, the graphs are based on experiments run for a period of six hours with six intervals of one hour each. The data supporting the graph of FIG. 5C is set forth in Table X as follows:

TABLE X

| Composition Tested | Reference Numeral For Graph | Insects Per Interval (Two Hour Intervals Totalling Twelve Hours) | | | | | |
|---|---|---|---|---|---|---|---|
| (AEDES AEGYPTI) | | | | | | | |
| ORANGE FLOWER ETHER | 503C | 0 | 11 | 24 | 77 | 50 | 167 | 167 |
| PAMPLE FLEUR ® | 504C | 0 | 8 | 9 | 9 | 0 | 3 | 2 |
| VIOLIFF TM | 505C | 0 | 0 | 6 | 0 | 3 | 1 | 5 |
| geraniol coeur | 506C | 0 | 7 | 3 | 10 | 7 | 2 | 0 |
| Air | 502C | 0 | 248 | 283 | 291 | 287 | 318 | 354 |

Referring to FIG. 5D, the graphs are based on experiments run for a period of one hour with six intervals of ten minutes each. The data supporting the graph of FIG. 5D is set forth in the following Table XI:

TABLE XI

| Composition Tested | Reference Numeral For Graph | Insects Per Interval (Two Hour Intervals Totalling Twelve Hours) | | | | | |
|---|---|---|---|---|---|---|---|
| (AEDES AEGYPTI) | | | | | | | |
| ORANGE FLOWER ETHER | 503D | 0 | 7 | 32 | 5 | 15 | 1 | 0 |
| PAMPLE-FLEUR ® | 504D | 0 | 10 | 0 | 3 | 25 | 3 | 0 |
| VIOLIFF TM | 505D | 0 | 2 | 8 | 2 | 0 | 0 | 0 |
| geraniol coeur | 506D | 0 | 3 | 0 | 0 | 0 | 0 | 0 |
| Air | 502D | 0 | 2 | 30 | 53 | 6 | 329 | 277 |

Referring to FIG. 5E, the graphs are based on experiments run for a period of six hours with six intervals of one hour each. The data supporting the graph of FIG. 5E is set forth in Table XII as follows:

TABLE XII

| Composition Tested | Reference Numeral For Graph | Insects Per Interval (Two Hour Intervals Totalling Twelve Hours) | | | | | |
|---|---|---|---|---|---|---|---|
| (AEDES AEGYPTI) | | | | | | | |
| ORANGE FLOWER ETHER | 503E | 0 | 0 | 1 | 1 | 20 | 22 | 60 |
| PAMPLE-FLEUR ® | 504E | 0 | 0 | 3 | 0 | 0 | 0 | 0 |
| VIOLIFF TM | 505E | 0 | 0 | 0 | 0 | 18 | 0 | 0 |
| geraniol coeur | 506E | 0 | 0 | 0 | 0 | 0 | 0 | 0 |
| Air | 502E | 0 | 277 | 31 | 94 | 109 | 259 | 169 |

Regardig FIG. 6, FIG. 6 is a schematic cut-away elevation diagram of an extrusion and pelletizing apparatus useful for the fabrication of matrix 26 used in carrying out a process of our invention. The operation of the apparatus causes an insect attractant or repellent to be incorporated into a polymer such as a polyethylene. Motor 215 drives the extruder screws located at 223a in barrel 216a, the extruder being operated at temperatures in the range of from about 150° C. up to about 250° C. At the beginning of the barrel, resin at source 212 together with additives, e.g., processing aides and densifiers at location 213 is added via addition funnel 214 into the extruder. Simultaneously (when the operation reaches "steady state"), insect repellent, e.g., the PAMPLEFLEUR ® having the structure:

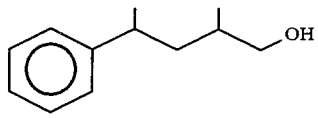

of our invention is added to the extruder at one or more barrel segments, S-3, S-4, S-5, S-6, S-7 and S-8 of the extruder (which may be a twin screw or single screw extruder) at locations 218a, 218b, 218c, and 218d (for example) by means of gear pump 223 from source 217. From source 219 into barrel segements S-5, S-6, S-7, S-8, S-9 and S-10, a gaseous liquid blowing agent, e.g., nitrogen, carbon dioxide and the like are added simultaneously with the addition of insect repellent, e.g., the PAMPLEFLEUR ® of our invention. The feed rate range of resin is about 80–300 pounds per hour. The feed rate range of insect repellent is between 1 and 35% of the feed rate range of the resin. The blowing agent range is such that the pressure of the gas or the pressure over the liqui being fed into the extruder is between about 50 and 200 psig if, indeed, blowing agent is added. If desired the extruded ribbon or cylinder may be passed through water bath 220 and pelletizer 221 into collection apparatus 221a.

A preferred embodiment of our invention set forth in FIGS. 7-16 comprises an ellipsodially shaped detergent tablet 830 containing a solid plastic core 832 which can be fabricated from, for example, polyethylene, polypropylene, nylon or any polymer capable of having therein microvoids from which an insect repelling substance, e.g., the PAMPLEFLEUR ® of our invention will be controllably transported from the plastic core into and through the soap cake over a reasonable period of time during the use of the soap cake. Such soap cake can be used in a washing procedure by an individual as during a shower. Immediately subsequent to the shower and for a period of ten hours, insect repellency will be had against house flies, mosquitoes and horn flies when using the esters, alcohols or ether of our invention. Such polymers can be microporous polymers such as those described in U.S. Pat. No. 4,247,498 issued on Jan. 27, 1981, the specification for which is incorporated hereby by reference. Surrounding the central plastic core containing insect repellent 832 as detergent 830 which is in the solid phase at ambient conditions, e.g., room temperature and atmospheric pressure. Examples of workable detergents 830 are "elastic" detergents such as those described in U.S. Pat. No. 4,181,632 issued on Jan. 1, 1980, the disclosure of which is incorporated by reference herein, or "transparent" soaps such as those set forth in U.S. Pat. No. 4,165,293 issued on Aug. 21, 1979, the disclosure of which is incorporated by reference herein. Other examples of the detergent 830 useful in our invention are those set forth as "variegated soaps" in Canadian Letters Patent No. 1,101,165 issued on May 19, 1981.

On use of the soap tablet 830 or detergent bar, the insect repellent agent, e.g., one or more of the esters, alcohols or ether of our invention originally located in plastic core 832 as transported at a steady state from core 832 through core surface 831 through the detergent 830 and finally through the surface of the detergent bar at, for example, 833, 834, 835 and 836.

The detergent bar or tablet 830 of our invention may be of any geometric shape, for example, a rectangular parallelpiped tablet as shown in FIGS. 11, 12 and 13 containing solid plastic core 839. The insect repellent located in solid plastic core 839 on use of the detergent bar passes through at a steady state, surface 832 of FIG. 12, detergent 838 and finally surface 839 at, for example, locations 840, 841, 842 and 843. The environment surrounding the detergent bar on use thereof is then treated with insect repellent, e.g., PAMPLEFLEUR ® or INDISAN TM, at 833, 844 and 845. Optionally, aromatizing agent (other than the alcohols, esters or ether of our invention) can also be contained in the detergent bar and so the environment surrounding the detergent bar on use thereof (in a washing procedure by a person) would also be aesthetically aromatized at 843, 844 and 845, for example.

As shown in FIGS. 14, 15 and 16, the plastic core of the detergent tablet 830 may have a single finite void at its center 851 (of FIGS. 15 and 16) in which the insect repellent agent and optionally the aromatizing agent is contained. The plastic core is a shell 848 having outer surface 852 (shown in FIGS. 15 and 16). The insect repellent agent (and, optionally the additional aromatizing agent) contained in the void in the plastic core permeates through shell 848, past surface 852 at a steady state through the detergent 847 and to the environment at, for example, 856, 857, 858 and 859.

In addition tot he insect repellent contained in the core, e.g., core 839 or core void the core can also contain other materials, for therapeutic use, for example, bacteriostats, deodorizing agents and the like which are compatible with the insect repellents, the esters, alcohols and ether of our ivention, e.g., ORANGE FLOWER ETHER having the structure:

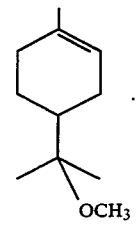

In the alternative, the plastic core of the detergent tablet of FIGS. 14, 15 and 16 may have an empty single finite void at its center 851 with the insect repellent contained in the shell 848.

At the end of the use of the detergent tablet, the hollow core or the solid core can be used as an insect repelling and aroma imparting air freshener household article. In addition, depending on the ratio of the volume of the void 851, to the solid part of the detergent tablet of FIGS. 14, 15 and 16, the detergent tablet of FIGS. 14, 15 and 16 can be so fabricated that it will float on the surface of the liquid in which it is being used and this physical attribute has certain obvious advantages.

FIGS. 17, 18, 19 and 20 are bar graphs setting forth the relative attractancy or repellency of certain compositions when tested in the field olfactometer of our invention of FIG. 1. The "x" axis of each of the graphs sets forth the mean number of mosquitoes, to wit:

(a') *Aedes aegypti;*
(b') *Aedes albopictus;*
(c') Anopheles spp.;
(d') Culex spp.;
(e') Aedes spp.;
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian* trapped. The "x" axis sets forth the treatment composition.

Referring to FIG. 17, the bar indicated by reference numeral 1700 shows attractancy by a 50:50 mixture of air and $CO_2$ with a feed rate of $CO_2$ being 2.71 gram moles per hour. The bar indicated by reference numeral 1702 is for VIOLIFF TM. The bar indicated by reference numeral 1704 is for PAMPLEFLEUR ®.

The apparatus of FIG. 1 has six infrared light emitting diodes.

Referring to FIG. 18, the bar indicated by reference numeral 1800 is for a 50:50 mole:mole mixture of air and $CO_2$ with a feed rate of $CO_2$ being 2.71 gram moles per hour. The bar indicated by reference numeral 1802 is for INDISAN TM.

The apparatus used for the purposes of creation of the data for FIG. 18, the apparatus of FIG. 1 has three infrared light emitting diodes.

Referring to FIG. 19, the bar indicated by reference numeral 1900 is for a 50:50 mole:mole mixture of air and $CO_2$ with the feed rate of $CO_2$ being 2.71 gram moles per hour. The bar indicated by reference numeral 1902 is for VIOLIFF ™. This graphs shows that VI-OLIFF ™ is a repellent for the species:

(a') *Aedes aegypti;*
(b') *Aedes albopictus;*
(c') *Anopheles* spp.;
(d') *Culex* spp.;
(e') *Aedes* spp.;
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian* and the mixture of $CO_2$ and air is an attractant for the insect species:

(a') *Aedes aegypti;*
(b') *Aedes albopictus;*
(c') *Anopheles* spp.;
(d') *Culex* spp.;
(e') *Aedes* spp.;
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian.*

The apparatus of FIG. 1 for the purposes of creation of the data for FIG. 19 has six infrared light emitting diodes.

With respect to FIG. 20, the bar indicated by reference numeral 2000 is for a 50:50 mole:mole mixture of air and $CO_2$ with a feed rate of $CO_2$ being 2.71 gram moles per hour. The bar indicated by reference numeral 2002 is for PAMPLEFLEUR ®. The bar indicated by reference numeral 2004 is for geraniol. The apparatus of FIG. 1 for the purposes of creation of the data for FIG. 20 has twelve infrared light emitting diodes. The data shows that the mixture of air and $CO_2$ is an attractant for the insect species:

(a') *Aedes aegypti;*
(b') *Aedes albopictus;*
(c') *Anopheles* spp.;
(d') *Culex* spp.;
(e') *Aedes* spp.;
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian* and is repellent for PAMPLEFLEUR ® and geraniol coeur with respect to the insect species:

(a') *Aedes aegypti;*
(b') *Aedes albopictus;*
(c') *Anopheles* spp.;
(d') *Culex* spp.;
(e') *Aedes* spp.;
(f') *Culex nigripalpus;*
(g') *Aedes atlanticus;*
(h') *Culex salinarius;*
(i') *Aedes vexans;*
(j') *Aedes infirmatus;* and
(k') *Anopheles crucian.*

FIG. 21 is the GLC profile for the reaction product prior to distillation of Example V. Reference numeral "1" represents the peak for methyl alcohol. Reference numeral "2" represents the peak for 4-cyclooctenyl formate that is not reacted. Reference numeral "3" represents the peak for 4-cyclooctenyl methyl carbonate having the structure:

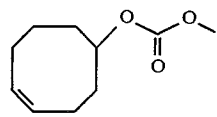

The following examples set forth processes for carrying out our invention by means of repelling certain species of insects from three dimensional spaces inhabitable by such insects. The examples are not intended to be limiting and the invention is only to be limited by the claims. Unless otherwise indicated all parts and percentages are by weight.

EXAMPLE I

| EXAMPLE I PARAFFIN WAX CANDLE BODY | |
| --- | --- |
| Ingredients | Parts by Weight |
| Paraffin wax | 95.0 |
| PAMPLEFLEUR ® having the structure: 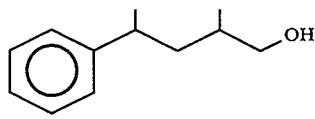 | 3.0 |
| ORANGE FLOWER ETHER having the structure: 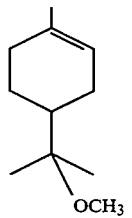 | 2.0 |

The paraffin wax is intimately admixed at 150° C. and 10 atmospheres pressure with the ORANGE FLOWER ETHER and PAMPLEFLEUR ® in an autoclave wth intensive shaking. The autoclave pressure is maintained with a nitrogen atmosphere. At the end of the period of one hour the autoclave is depressurized, the autoclave is opened and the resulting mixture is poured into cylindrical candle molds containing wicks.

The resulting candles on use evolve an aesthetically pleasing aroma and, in addition, give rise to efficacious house fly repellency. The candles are effective in preventing house flies from entering a room in which one candle is burning for a period of 10 minutes, the said room having dimensions of 6'×15'×15' having a 3'×3' open portal adjacent to a house fly-infested region in the month of August in Highlands, N.J., next to a very swampy area.

EXAMPLE II

A transparent candle base is produced by intimately admixing the following ingrediens:

| Ingredients | Parts by Weight |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® 60 | 1.5 |
| Isopropyl Isostearate | 4.0 |
| Isopropyl Myristate | 4.0. |

The foregoing mixture is placed in an autoclave and intimately admixed with a perfume-scent repellent composition containing VIOLIFF ™ prepared according to the process of Example V, infra and containing a major proportion of the compound having the structure:

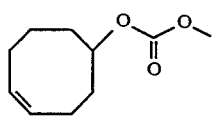

and a minor proportion of the compound having the structure:

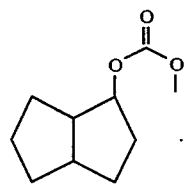

The VIOLIFF ™ is incorporated at the rate of 8% by weight of the total candle base composition.

The autoclave is sealed and heated to 180° C. under 15 atmospheres pressure and maintained with vigorous shaking for a period of five hours. At the end of the five hour period, the autoclave is depressurized (being under a nitrogen pressure atmosphere) and the autocalve is opened and the contents are then poured into cylindrical candle molds 4" in height and 2" in diameter containing 0.125' wicks. The resulting candles have efficacious insect repellencies and have aesthetically pleasing aromas on use.

The candles are effective in preventing the following insects:

(a) *Musca domestica* L.(Diptera:Muscidae);
(b) *Aedes aegypti;*
(c) *Aedes albopictus;*
(d) Anopheles spp.;
(e) *Coquillettidia perturbans;*
(f) Cullseta spp.;
(g) Culex spp.;
(h) Psorophora spp.;
(i) Culicoides spp.; and/or
(j) Lutzomyia spp.;
(k) Aedes spp.;
(l) *Culex nigripalpus;*
(m) *Aedes atlanticus;*
(n) *Culex salinarius;*
(o) *Aedes vexans;*
(p) Simuliidae spp.;
(q) *Psorophora ferox;*
(r) *Aedes infirmatus;*
(s) *Drosophila melanogaster;*
(t) Coccinellidae;
(u) *Anopheles crucian;*
(v) *Psorophora columbiae;* and
(w) *Haemotobia irritans* (L.)

from entering a room in which two candles have been burning for 15 minutes. The said room having dimensions of 6'×15'×15' and having a 3'×3' open portal adjacent a house fly, horn fly and mosquito infested region in Highlands, N.J., in the month of August in the temperate zone.

EXAMPLE III

The following candle base composition of matter is prepared:

| Ingredients | Parts by Weight |
|---|---|
| Polyamide (VERSAMID ® 940 manufactured by the Henkel Chemical Corporation of Minneapolis, Minnesota) | 30.0 |
| Stearic acid | 5.0 |
| Methyl-12-hydroxy stearate | 5.0 |
| 10 Carbon primary alcohol manufactured by the (Continental Oil Company); ALFOL ® 10); (ALFOL ® is a trademark of Conoco Division of E. I. DuPont of Wilmington, Delaware | 5.0 |
| Myristyl Myristate | 10.0 |
| Stearic hydrazide | 0.1 |
| Diethyl phthalate | 2.0 |
| INDISAN ™ | 3.0 |
| Light White Mineral Oil | q.s. to 100% |

All of the materials except the polyamide are mixed at room temperature. The mixture i s then heated gradually with gradual addition of the polyamide and with agitation beginnin with the commencement of addition of the polyamide. In the proportion required, the polyamide doe s not become fully soluble until the mixture reaches the temperature of about 220° F. The temperature on the order of 220° F. to 230° F. is maintained at atmospheric pressure with continued agitation until the polyamide is fulloy dissolved. Since higher temperatures promote solution of the polyamide this temperature range can be slightly exceeded with some advantage. As soon as the polyamide has dissolved completely, the mixture is poured into molds following the conventional practice in the manufacture of molded candles. As the candles cool they harden. The candles are then freed from the molds and tested for insect repellency.

The candles are effective in preventing the following insects from entering a room in which two candles have been burning for 15 minutes, the said room having dimensions of 6'×15'×15' and having a 3'×3' open portal adjacent to an insect infested region in the month of August in Highlands, N.J.:

(a) *Musca domestica* L.(Diptera:Muscidae);
(b) *Aedes aegypti;*
(c) *Aedes albopictus;*
(d) Anopheles spp.;
(e) *Coquillettidia perturbans;*
(f) Cullseta spp.;
(g) Culex spp.;
(h) Psorophora spp.;
(i) Culicoides spp.; and/or (j) *Lutzomyia* spp.;
(k) *Aedes* spp.;
(l) *Culex nigripalpus;*
(m) *Aedes atlanticus;*
(n) *Culex salinarius;*
(o) *Aedes vexans;*
(p) *Simuliidae* spp.;
(q) *Psorophora ferox;*
(r) *Aedes infirmatus;*
(s) *Drosophila melanogaster;*
(t) *Coccinellidae;*
(u) *Anopheles crucian;*
(v) *Psorophora columbiae;* and
(w) *Haemotobia irritans* (L.).

EXAMPLE IV

A study was conducted to evaluate the efficacy of candles which are designated "A", "B", and "C" mn repelling house flies (*Musca domestica* L.(Diptera:Muscidae)).

Candle "A" contained 95% Paraffin Wax and 5% of the following composition:
100 Parts by weight of VIOLIFF TM; and
700 Parts by weight of a perfume composition containing the following ingredients:

| Ingredients | Parts by Weight |
| --- | --- |
| (i) Perfume mixture of essential grams oils and chemicals, to with the methyl ester of 2,5-dihydroxy-4-6-dimethyl benzoic acid; dihydro myrcenol; oakmoss absolute; benzyl acetate; geraniol; isobornyl acetate; citronellyl acetate; para-t-butyl phenyl isovaleraldehyde; benzyl slicylate; hexyl cinnamic aldehyde; geranonitrile; patchouli oil; alpha-terpineol; tetrahydromuguol; phenyl ethyl alcohol; cedrenal; methyl ionone; cinnamyl acetate; benzyl benzoate | 83.8 |
| (ii) Solvent: the methyl ester of dihydroabietic acid | 4.00 |

Candle "B" contained 90% Paraffin Wax and 10% citronella oil.

Candle "C" contained only Paraffin Wax.

The candles are allowed to burn for 20 minutes and the number of house flies repelled from a house fly-infested room is recorded for the next 60 minutes with the following equipment and procedure:

MATERIALS

Test Chamber

The evaluation was conducted in a 28.3 cubic meter chamber with airing ports. A screened cage measuring 15 cm × 15 cm × 47.5 cm was attached inside an upper airing port, and a screened repellency observation cage measuring 15 cm × 15 cm × 32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged mouse was used as an attractant and was placed inside the chamber in the larger section of the repellency cage.

Test Insect

Adult house flies (*Musca domestica*) are test insects.

PROCEDURE

For each replicate, 75 to 100 adult house flies were removed from the rearing cage by means of a vacuum aspirator, and transferred by carbon dioxide anesthesia to the inner cage containing the mouse. The assembled cage was placed in one of the upper ventilation ports of the chamber.

For each experimental situation the test insects were transferred to a clean cage containing the mouse. A house fly candle was placed centrally on the chamber floor and burned for 20 minutes before initiating the repellency counts. The maximum period for the repellency counts was 60 minutes. The first repellency count was made at 10 minutes after the burning ended, and subsequent counts were taken at 5-minute intervals thereafter. The number of house flies repelled were those escaping to the outside cage. For the control counts were made in a similar manner, but no candle was burned.

The same three candles were used for all four replicates. Between replicates the chamber was exhausted, the Kraft paper flooring for the chamber was replaced, and the two screened repellency cages were submerged in hot detergent water, rinsed and dried.

RESULTS

The average percent of house flies repelled for each 5-minute exposure period through 60 minutes is reported in the following Table XIII:

TABLE XIII

| | | | House Flies Repelled At Five Minute Time Intervals 20 Minutes Post Exposure | | | | | | | | | | |
| --- | --- | --- | --- | --- | --- | --- | --- | --- | --- | --- | --- | --- | --- |
| | | Number of | Cumulative Number of House Flies Repelled at Indicated Minutes | | | | | | | | | | Overall |
| SAMPLE: | Replicate | House Flies | 10 | 15 | 20 | 25 | 30 | 35 | 40 | 45 | 50 | 55 | 60 | Percent |
| Untreated | 1 | 93 | 1 | 1 | 1 | 1 | 1 | 2 | 2 | 3 | 3 | 4 | 6 | 6.45 |
| (no candle | 2 | 67 | 0 | 1 | 2 | 3 | 5 | 6 | 6 | 6 | 6 | 7 | 7 | 10.45 |
| used) | 3 | 86 | 2 | 2 | 2 | 3 | 4 | 6 | 6 | 7 | 7 | 7 | 7 | 8.14 |
| | 4 | 90 | 2 | 3 | 3 | 3 | 3 | 4 | 5 | 5 | 5 | 5 | 5 | 5.56 |
| Total | | 336 | 5 | 7 | 8 | 10 | 13 | 17 | 19 | 21 | 21 | 23 | 25 | |
| Average Percent | | | 1 | 2 | 2 | 3 | 4 | 5 | 6 | 6 | 6 | 7 | 7 | 7.44 |
| A | 1 | 108 | 2 | 5 | 7 | 8 | 8 | 8 | 8 | 10 | 10 | 10 | 12 | 11.11 |
| | 2 | 95 | 0 | 5 | 5 | 6 | 7 | 7 | 9 | 11 | 12 | 12 | 16 | 16.84 |
| | 3 | 86 | 3 | 6 | 8 | 8 | 10 | 10 | 11 | 11 | 12 | 12 | 13 | 15.12 |
| | 4 | 96 | 2 | 3 | 5 | 6 | 9 | 11 | 11 | 14 | 16 | 17 | 17 | 17.71 |
| Total | | 385 | 7 | 19 | 25 | 28 | 34 | 36 | 39 | 46 | 50 | 51 | 58 | |
| Average Percent | | | 2 | 5 | 6 | 7 | 9 | 9 | 10 | 12 | 13 | 13 | 15 | 15.06 |

TABLE XIII-continued

House Flies Repelled At Five Minute Time Intervals
20 Minutes Post Exposure

| SAMPLE: | Replicate | Number of House Flies | Cumulative Number of House Flies Repelled at Indicated Minutes | | | | | | | | | | | Overall Percent |
|---|---|---|---|---|---|---|---|---|---|---|---|---|---|---|
| | | | 10 | 15 | 20 | 25 | 30 | 35 | 40 | 45 | 50 | 55 | 60 | |
| B | 1 | 80 | 4 | 5 | 7 | 7 | 8 | 8 | 9 | 9 | 9 | 10 | 11 | 13.75 |
| | 2 | 100 | 2 | 4 | 5 | 6 | 7 | 10 | 11 | 11 | 11 | 12 | 12 | 12.00 |
| | 3 | 87 | 2 | 2 | 3 | 4 | 5 | 5 | 6 | 6 | 6 | 6 | 7 | 8.04 |
| | 4 | 91 | 2 | 4 | 5 | 6 | 6 | 6 | 7 | 7 | 7 | 9 | 10 | 10.99 |
| Total | | 358 | 10 | 15 | 20 | 23 | 26 | 29 | 33 | 33 | 33 | 37 | 41 | |
| Average Percent | | | 3 | 4 | 6 | 6 | 7 | 8 | 9 | 9 | 9 | 10 | 11 | 11.45 |
| C | 1 | 79 | 6 | 8 | 8 | 8 | 8 | 8 | 8 | 8 | 8 | 9 | 10 | 12.66 |
| | 2 | 86 | 3 | 5 | 5 | 6 | 6 | 6 | 6 | 6 | 7 | 7 | 8 | 9.30 |
| | 3 | 92 | 2 | 4 | 4 | 5 | 7 | 7 | 7 | 7 | 7 | 7 | 8 | 8.70 |
| | 4 | 91 | 0 | 1 | 1 | 2 | 2 | 2 | 4 | 6 | 7 | 7 | 9 | 9.89 |
| Total | | 348 | 11 | 18 | 18 | 11 | 23 | 23 | 25 | 27 | 29 | 30 | 35 | |
| Average Percent | | | 3 | 5 | 5 | 6 | 7 | 7 | 7 | 8 | 8 | 9 | 10 | 10.06 |

The results of this experiment show that the candle containing the VIOLIFF TM composition (2.5% of the total weight) is about 40% more efficacious from an insect repellency standpoint than a candle containing 10% citronella oil . . . and in addition, such candles containing the VIOLIFF TM composition on burning yield an aesthetically pleasing scent which is totally unlike the 10% citronella oil containing candle which yields an aesthetically displeasing scent.

EXAMPLE II

Preparation of Composition Containing Major Proportion of 4-Cyclooctenyl Methyl Carbonate (VIOLIFF TM)

Into a 5-liter reaction flask equipped with heating mantle, stirrer, Bidwell trap, addition funnel, thermometer, reflux condenser and nitrogen blanket apparatus, are placed 2 liters (22.0 moles) of dimethyl carbonate and 81 grams (1.5 moles) of powdered sodium methoxide. The resulting mixture is heated to 65° C. and over a period of 4 hours while maintaining the temperature of the mixture at 60°-65° C. 1,719 grams (11.0 moles) of the composition containing a preponderance of 4-cyclooctenyl formate produced according to Example I (bulked distillation Fractions 5, 7 and 9) of U.S. Pat. No. 4,452,730 issued on Jun. 5, 1984 is added to the reaction mass while recovering methyl formate reaction product via the Bidwell trap. After addition is complete, the reaction mass is heated to 70° C. in order to remove the remaining the remaining formate reaction product.

The reaction mass is then washed with two 500 ml portions of saturated sodium chloride and distilled on a 1″ Goodloe column yielding the following fractions:

| Fraction Number | Vapor Temp. (°C.) | Liquid Temp. (°C.) | Pressure mm/Hg. | Reflux Ratio | % of 4-cyclooctenyl Methyl Carbonate | Weight of Fraction (grams) |
|---|---|---|---|---|---|---|
| 1 | 48/64 | 89/95 | 1.8/3.0 | 4:1 | — | — |
| 2 | 62 | 97 | 1.4 | 4:1 | — | — |
| 3 | 70 | 100 | 2.6 | 4:1 | — | — |
| 4 | 77 | 100 | 1.4 | 4:1 | — | — |
| 5 | 72/87 | 95/98 | 2.3 | 9:1 | 78.0 | — |
| 6 | 9-02 | 112/105 | 6.5 | 4:1 | 93.0 | 52 |
| 7 | 92 | 107 | 4.6 | 4:1 | 97.0 | 88 |
| 8 | 92 | 107 | 4.0 | 4:1 | — | 112 |
| 9 | 86 | 110 | 3.0 | 4:1 | 98.0 | 119 |
| 10 | 86 | 113 | 3.0 | 4:1 | — | 113 |
| 11 | 86 | 115 | 3.0 | 4:1 | 98.8 | 130 |
| 12 | 86 | 116 | 3.0 | 4:1 | — | 55 |
| 13 | 86 | 118 | 3.0 | 4:1 | 99.8 | 101 |
| 14 | 86 | 120 | 3.0 | 4:1 | — | 65. |

Fractions 7-14 are bulked for the purpose of organoleptic evaluation.

FIG. 21 is the GLC profile for the reaction product prior to distillation. The numeral "1" represents the peak for methyl alcohol. The numeral "2" represents the peak for 4-cyclooctenyl formate that is not reacted. The reference numeral "3" represents the peak for the 4-cyclooctenyl methyl carbonate reaction product having the structure:

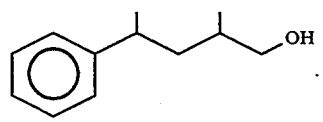

FIG. 22 is the GLC profile for Fraction 13 of the foregoing distillation containing a major proportion of the compound having the structure:

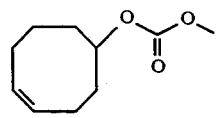

as well as a minor proportion of the compound having the structure:

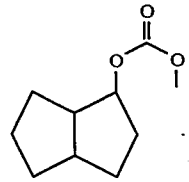

FIG. 23 is the NMR spectrum for Fraction 13 of the foregoing distillation containing a major proportion of the compound having he structure:

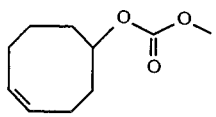

as well as a minor proportion of the compound having the structure:

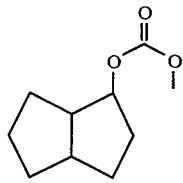

(Solvent: CFCl₃; Field Strength: 100 MHz).

FIG. 24 is the infrared spectrum for Fraction 13 of the foregoing distillation containing a major proportion of the compound having the structure:

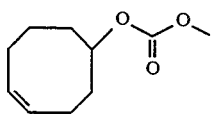

as well as a minor proportion of the compound having the structure:

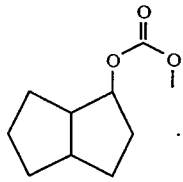

FIG. 25 is the GLC profile for Fraction 7 of the foregoing distillation containing a major proportion of the compound having the structure:

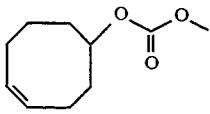

and a minor proportion of the compound having the structure:

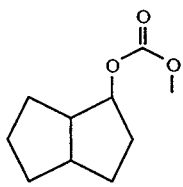

(ratio of compound having the structure:

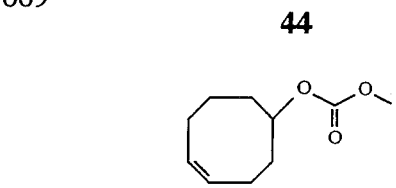

to compound having the structure:

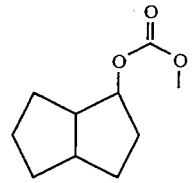

is 77:19).

FIG. 26 is the NMR spectrum for Fraction 7 of the foregoing distillation containing the compound having the structure:

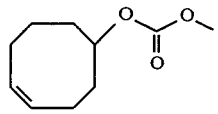

in major proportion and the compound having the structure:

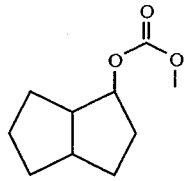

in minor proportion ( Solvent: CFCl₃; Field Strength: 100 MHz).

FIG. 27 is the infrared spectrum for Fraction 7 of the foregoing distillation containing a major proportion of the compound having the structure:

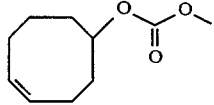

and a minor proportion of the compound having the structure:

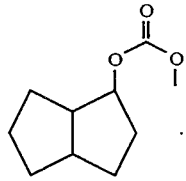

Bulked distillation Fractions 7-14 have a fruity (pear, banana), sweet, violet-like, green and cucumber aroma profile. In addition bulked Fractions 7-14 have the ability to repel each of the species of the following insects:

(a) *Musca domestica* L.(Diptera:Muscidae);

(b) *Aedes aegypti;*
(c) *Aedes albopictus;*
(d) Anopheles spp.;
(e) *Coquillettidia perturbans;*
(f) Culiseta spp.;
(g) Culex spp.;
(h) Psorophora spp.;
(i) Culicoides spp.; and/or
(j) Lutzomyia spp.;
(k) Aedes spp.;
(l) *Culex nigripalpus;*
(m) *Aedes atlanticus;*
(n) *Culex salinarius;*
(o) *Aedes vexans;*
(P) Simuliidae spp.;
(q) *Psorophora ferox;*
(r) *Aedes infirmatus;*
(s) *Drosophila melanogaster;*
(t) Coccinellidae;
(u) *Anopheles crucian;*
(v) *Psorophora columbiae;* and
(w) *Haemotobia irritans* (L.).

EXAMPLE VI

Preparation of Meta(Iso-Camphyl-5)-Cyclohexanol

STAGE 1

Into a 1 liter autoclave is placed the following materials:

| | |
|---|---|
| Reaction product of catehol and camphene produced according to Example XI (Fractions 3–13) of U.S. Letters Pat. No. 4,014,944 issued on March 27, 1977, the specification for which is incorporated by reference herein | 397 grams |
| Isopropyl alcohol | 100 ml |
| Raney Nickel | 30 grams. |

After sealing, the autoclave is then purged with nitrogen followed by hydrogen. The autoclave is pressurized with hydrogen to 500 psig and heated to 100° C., at which temperature stirring is commenced. The autoclave is then heated up to a temperature of less than 160° C. for the major portion of the time of the 1st stage of hydrogenation. However, as the uptake of hydrogen diminishes, the autoclave is heated to a temperature of 205° C. A table showing the time, temperature hydrogenation, autoclave pressure, reservoir pressure, pressure drop and total pressure drop is set forth below:

| Time | Temperature (°C.) | Autoclave (psig) | Reservoir Pressure (psig) | Pressure Drop (psig) | Total Pressure Drop (psig) |
|---|---|---|---|---|---|
| 0920 | 75 | 500 | 2010 | — | — |
| 0947 | 110 | 540 | 2010 | — | — |
| 0952 | 125 | 340 | 2010 | — | — |
| 1017 | 110 | 500 | 850 | 1160 | 1160 |
| 1030 | 125 | 500 | 580 | 170 | 1430 |
| 1030 | 125 | 500 | 2010 | — | — |
| 1045 | 145 | — | — | — | — |
| 1055 | 180 | 500 | 600 | 1410 | 2840 |
| 1055 | 180 | 480 | 2010 | — | — |
| 1205 | 160 | 500 | 680 | 1330 | 4170 |
| 1205 | 160 | 480 | 2000 | — | — |
| 1240 | 170 | 480 | 1620 | 380 | 4550 |
| 1317 | 195 | 480 | 1430 | — | — |
| 1533 | 205 | 500 | 1130 | — | — |
| 1616 | 205 | 480 | 1120 | 500 | 5050 |
| 1920 | 90 | 150 | — | — | —. |

At the end of the period of 10 hours as is set forth in the above table, the autoclave is opened and the reaction mass is filtered. The autoclave is then rinsed twice with isopropyl alcohol. The solvent is stripped off at 110° C. and atmospheric pressure, then at 25 mm/Hg. at 11-° C. At this point IR and GLC analysis indicates that the reaction mass is a mixture of compounds having the structure:

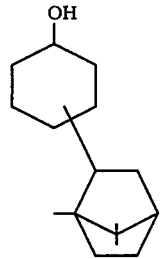

STAGE 2

The solvent-stripped reaction product of the first stage of hydrogenation is admixed with 30 grams of Raney nickel and 100 grams of isopropyl alcohol and replaced into the 1 liter autoclave. After sealing, the autoclave is purged with nitrogen followed by hydrogen. The autoclave is then heated to 217° C. and held at 225°–230° C. and 500 psig for a period of eight hours. At the end of the eight hour period, the reaction mixture is cooled, the autoclave is opened and the reaction mass is removed from the autoclave, filtered and the isopropanol recovered at atmospheric pressure at 100° C. then at 25 mm/Hg. at 110° C. 19.5 Grams of Primol is added to the resulting oil which is then distilled on a 6" vigreaux column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 113 | 148 | 2.3 | 4.9 |
| 2 | 146 | 165 | 3.5 | 17.4 |
| 3 | 139 | 165 | 2.7 | 12.4 |
| 4 | 145 | 170 | 2.7 | 11.6 |
| 5 | 147 | 175 | 2.7 | 14.0 |
| 6 | 154 | 175 | 2.7 | 15.5 |
| 7 | 158 | 178 | 2.7 | 16.7 |
| 8 | 165 | 178 | 2.5 | 22.7 |
| 9 | 165 | 185 | 2.8 | 15.8 |
| 10 | 156 | 183 | 2.4 | 21.4 |
| 11 | 162 | 187 | 2.4 | 22.1 |
| 12 | 172 | 192 | 2.4 | 26.0 |
| 13 | 187 | 204 | 2.3 | 18.2 |
| 14 | 209 | 236 | 2.5 | 21.9 |
| 15 | 235 | 250 | 2.7 | 20.5 |
| 16 | 241 | 250 | 2.7 | 8.6. |

Fractions 6–14 are bulked and the resulting product has a strong sandalwood aroma with woody nuances.

The resulting product is a mixture of several chemical compounds containing in a major proportion the compound having the structure:

$$\text{structure with cyclohexane ring bearing HO- group, connected to } HC^5-CH_2^6-C^1H-C^2(CH_3)_2-C^4H(CH_3)$$

The GLC profile thereof is set forth in FIG. 29. The resulting material has the ability to repel the following species of insects from a three dimensional space inhabitable by such insects:

(a) *Musca domestica* L.(Diptera:Muscidae);
(b) *Aedes aegypti;*
(c) *Aedes albopictus;*
(d) *Anopheles spp.;*
(e) *Coquillettidia perturbans;*
(f) *Culiseta spp.;*
(g) *Culex spp.;*
(h) *Psorophora spp.;*
(i) *Culicoides spp.;* and/or
(j) *Lutzomyia spp.;*
(k) *Aedes spp.;*
(l) *Culex nigripalpus;*
(m) *Aedes atlanticus;*
(n) *Culex salinarius;*
(o) *Aedes vexans;*
(p) *Simuliidae spp.;*
(q) *Psorophora ferox;*
(r) *Aedes infirmatus;*
(s) *Drosophila melanogaster;*
(t) Coccinellidae;
(u) *Anopheles crucian;*
(v) *Psorophora columbiae;* and
(w) *Haemotobia irritans* (L.).

What is claimed is:

1. A semiochemical field trap for blood feeding arthropods comprising:
   (1) an upright vertically-disposed first hollow outer housing having substantially rigid arthorpod-impermeable first side walls, an upper arthropod-impermeable horizontal surface substantially entirely contiguous with said first side walls, and a substantially entirely open bottom having a substantially horizontal plane substantially perpendicular to the vertical axis of said first hollow outer housing;
   (2) located along an axis substantially perpendicular to the horizontal plane of said substantially entirely open bottom of said first outer housing, substantially parallel to the vertical axis of said first hollow housing and within said first hollow housing, a second inner hollow housing having a hollow interior, opposite open upper first and lower second ends, vertically-disposed rigid arthropod-impenetrable side walls, and a longitudinal dimension extending between the two ends, said upper first end being at a substantial distance below said upper substantially horizontal surface of said first outer housing;
   (3) extending outwardly from the said substantially vertically disposed side walls of the second inner hollow housing to the side walls of the first hollow outer housing at an angle of from about −5° up to about −40°, measured downwardly from the substantially horizontal plane of the open bottom of said first hollow outer housing, substantially rigid rib components which enable the fixed positioning of said inner hollow housing with respect to the positioning of and within said outer hollow housing;
   (4) completely encompassingly traversing in a substantially tight fitting manner the area between (i) the first side walls of said first outer hollow housing and (ii) the second side walls of said second inner hollow housing along the directional vectors of said rib components and in a curvilinear plane below and substantially contiguous to said rib components a continuous substantiall macroporous mesh substance having such a mesh size as to be impenetrable by arthropods sought to be entrapped, but pervious to gas and liquid and, in addition, radiation transmittable, and capable of supporting a matrix article containing sustainably releaseable semiochemical;
   (5) at least one semiochemical-containing matrix comprising a porous containment agent containing in the interstices thereof at least one semiochemical sustainably releasable therefrom, located on the upper surface of said macroporous mesh substance;
   (6) a substantially vertically disposed drive shaft supported for rotary motion about its axis, extending from below and into the hollow interior of said second inner hollow housing along the said longitudinal dimension thereof;
   (7) motor means connected to a first lower end of said drive shaft for rotating said drive shaft about its axis;
   (8) air flow creation means attached to a second upper end of said of said drive shaft, being of such a design whereby the rotation of said drive shaft directly causes the rotation of said air flow creation means and induces the flow of air from beneath said second inner hollow housing upwardly into the 3-space within said first hollow outer housing between the outer side wall of the second inner hollow housing, and the inner side wall of said first outer hollow housing;
   (9) radiation emission means for emission of radiation of a specific wave length or of a range of wave lengths outwardly from the apparatus located in the vicinity of the lower portion of said second inner hollow housing, below the location of said rib components;
   (10) radiation pulsing means connected to said radiation means causing said radiation to have a frequency mimicking insect wing beat and/or insect visual sensing frequencies;
   (11) at least one power supply means associated with said trap energizing said radiation means, said radiation pulsing means and said motor means;

whereby; on engagement of the power supply means with said motor means, said radiation pulsing means, said radiation emission means, arthropods in the vicinity of said trap are attracted by said radiation to a location so close to said trap that in the event that an attracting semiochemical in said matrix is detected by said arthropods, said arthropods will enter the air stream created by said air flow creation means and be carried into the 3-space within said first hollow outer housing between the outer side wall of said second inner hollow housing and the inner side wall of said first outer hollow housing.

2. The semiochemical field trap for blood feeding arthropods of claim 1 additionally comprising:

(11) a carbon dioxide gas supply means for supplying gaseous carbon dioxide to the proximity of the lower portion of said second inner hollow housing, below the location of said rib components, simultaneously with the operation of said power supply means.

3. A semiochemical field trap for blood feeding arthropods comprising:

(1) an upright hollow frustum of a cone or polyhedron having three or more gas and liquid-impervious sides, a gas and liquid-impervious top surface having surface having surface area $A_1$ and radius $R_1$ and a substantially entirely open bottom circumscribed by an outer rim, said bottom having area $A_2$ and radius $R_2$ with $A_1 < A_2$ and $R_1 < R_2$; the plane of said top surface being substantially parallel to the plane of said substantially entirely open bottom; the distance from said top surface to said bottom plane being $D_1$;

(2) located along an axis substantially perpendicular to said top surface of said upright hollow frustum, and said open bottom plane of said frustum, a hollow vertically-disposed open-ended cylinder having height $D_3$ and radius $R_3$ having opposite open first and second ends, a gas and liquid-impervious side wall and a vertical longitudinal dimension extending between the two ends, said cylinder being substantially coaxial with said upright hollow frustum, a substantial portion of said cylinder being located between said upper surface of said frustum and said lower plane of said frustum, with said upper end of said cylinder being beneath and a finite distance $D_4$ from the upper surface of said frustum, with $R_3 < R_1$, $R_3 < R_2$ and $D_4 < D_1$;

(3) extending outwardly from the side wall of said cylinder at an angle of from $-5°$ down to $-40°$, subtended downwardly from the plane of the open bottom of said frustum with the vertex of the angle at said outer wall of said cylinder, substantially rigid rib components fixedly connecting the lower rim of said frustum to said side wall of said cylinder whereby said cylinder is fixedly positioned with reference to said frustum and is fixedly coaxial with said frustum;

(4) substantially completely encompassingly traversing in a tight fitting manner, the area between the vertical side wall of said cylinder and said outer rim of said frustum, along the directional vectors of, and in a curvilinear plane below and contiguous to said rib components, a continuous substantially monolaminar macroporous mesh substance having such a mesh size as to be impenetrable by arthropods sought to be entrapped but pervious to gas and liquid and being radiation transmittable, and being capable of supporting at least one substantially solid matrix article containing one or more substantially sustainably releasable semiochemical substances;

(5) at least one substantially solid semiochemical-containing matrix located on said monolaminar macroporous mesh substance containing a porous solid containing in the interstices thereof a semiochemical sustainably releasable from the solid matrix in a sustained release manner;

(6) a substantially vertically disposed drive shaft, having a first lower end and a second upper end, said drive shaft being coaxial with said open ended cylinder and being supported for rotary motion about its axis, said drive shaft, extending from below and into the hollow interior of said cylinder;

(7) motor means connected to said first lower end of said drive shaft for rotating said drive shaft;

(8) a propeller attached to said second upper end of said drive shaft, said propeller being rotatable in a plane substantially parallel to the plane of said open bottom of said frustum, and substantially perpendicular to the axis of said drive shaft, said propeller having an effective radius, $R_4$, with $R_4 < R_3$, whereby the rotation of said drive shaft rotates said propeller and induces a flow of air from beneath said cylinder, upwardly into the 3-space within said frustumn between the side wall of the cylinder and the side wall of said frustum;

(9) radiation means for emission of radiation of a wave length or a range of wave lengths outwardly from the trap, said radiation emission means being located in the proximity of the lower portion of said cylinder below the location of said substantially rigid rib components, the geometric configuation and location of said radiation emission means being such that at least a portion of the radiation generated by said radiation emission means reaches the curvilinear plane traversed by said macroporous mesh substance;

(10) radiation pulsing means connected to said radiation means causing said radiation to have a frequency mimicking insect wing beat and/or insect visual sensing frequencies;

(11) at least one electric power supply associated with said trap causing said radiation emission means to generate radiation and energizing said motor means and said radiation pulsing means;

whereby arthropods in the vicinity of said trap are attracted by radiation generated by said radiation emission means to a location so close to said trap that in the event an attractant in said matrix is detected by said arthropods, said arthropods will enter the upwardly moving air stream and be carried into the 3-space within said frustum between the wall of the cylinder and the side wall of said frustum.

4. The semiochemical field trap for blood feeding arthropods of claim 3 additionally comprising:

(12) a carbon dioxide gas supply means for supplying gaseous carbon dioxide to the proximity of the lower portion of said cylinder below the location of the substantially rigid rib components, simultaneously with the operation of said electric power supply means.

5. A semiochemical field trap for blood feeding arthropods comprising:

(1) an upright vertically-disposed first hollow outer housing having substantially rigid arthropod-impermeable first side walls, an upper arthropod-impermeable horizontal surface substantially entirely contiguous with said first side walls, and a substantially entirely open bottom having a substantially horizontal plane substantially perpendicular to the vertical axis of said first hollow outer housing;

(2) located along an axis substantially perpendicular to the horizontal plane of said substantially entirely open bottom of said first outer housing, substantially parallel to the vertical axis of said first hollow housing and within said first hollow housing, a second inner hollow housing having a hollow interior, opposite open upper first and lower second ends, vertically-disposed rigid arthropod-impenetrable side walls, and a longitudinal dimension extending between the two ends, said upper first end being at a substantial distance below said upper substantially horizontal surface of said first outer housing;

(3) extending outwardly from the said substantially vertically disposed side walls of the second inner hollow housing to the side walls of the first hollow outer housing at an angle of from about $-5°$ up to about $-40°$, measured downwardly from the substantially horizontal plane of the open bottom of said first hollow outer housing, substantially rigid rib components which enable the fixed positioning of said inner hollow housing with respect to the positioning of and within said outer hollow housing;

(4) completely encompassingly traversing in a substantially tight fitting manner the area between (i) the first side walls of said first outer housing and (ii) the second side walls of said second inner hollow housing along the directional vectors of said rib components and in a curvilinear plane below and substantially contiguous to said rib components, a continuous substantially macroporous mesh substance having such a mesh size as to be impenetrable by arthropods sought to be entrapped, but pervious to gas and liquid and, in addition, radiation transmittable;

(5) a substantially vertically disposed drive shaft supported for rotary motion about its axis, extending from below and into the hollow interior of said second inner hollow housing along the said longitudinal dimension thereof;

(6) motor means connected to a first lower end of said drive shaft for rotating said drive shaft about its axis;

(7) air flow creation means attached to a second upper end of said drive shaft, being of such a design whereby the rotation of said drive shaft directly causes the rotation of said air flow creation means and induces the flow of air from beneath said second inner hollow housing upwardly into the 3-space within said first hollow outer housing between the outer side wall of the second inner hollow housing and the inner side wall of said first outer hollow housing;

(8) radiation emission means for emission of radiation of a specific wave length or of a range of wave lengths outwardly from the apparatus located in the vicinity of the lower portion of said second inner hollow housing, below the location of said rib components;

(9) radiation pulsing means connected to said radiation means causing said radiation to have a frequency mimicking insect wing beat and/or insect visual sensing frequencies;

(10) at least one power supply means associated with said trap energizing said radiation emission means, said radiation pulsing means and said motor means.

6. The semiochemical field trap for blood feeding arthropods of claim 5 additionally comprising:

(11) a carbon dioxide gas supply means for supplying gaseous carbon dioxide to the proximity of the lower portion of the said second inner hollow housing, below the location of said rib components, simultaneously with the operation of said power supply means.

* * * * *